United States Patent [19]
Bernstein et al.

[11] Patent Number: 5,441,960
[45] Date of Patent: Aug. 15, 1995

[54] 1-PYRIMIDINYLACETAMIDE HUMAN LEUKOCYTE ELASTATE INHIBITORS

[75] Inventors: Peter R. Bernstein, Wallingford; Philip D. Edwards; Andrew Shaw, both of Kennett Square, all of Pa.; Royston M. Thomas, Macclesfield, England; Chris A. Veale, Newark, Del.; Peter Warner, Macclesfield; Donald J. Wolanin, Orange, Conn.

[73] Assignee: Zeneca Limited, London, England

[21] Appl. No.: 44,866

[22] Filed: Apr. 8, 1993

[30] Foreign Application Priority Data

Apr. 16, 1992 [GB] United Kingdom ............... 9208383
Aug. 14, 1992 [GB] United Kingdom ............... 9217367

[51] Int. Cl.$^6$ ................ A61K 31/505; C07D 239/22
[52] U.S. Cl. ........................ 514/269; 514/235.8; 544/123; 544/243; 544/295; 544/296; 544/319; 544/322; 544/333
[58] Field of Search .............. 514/235.8, 269; 544/123, 243, 295, 319, 322, 296, 333

[56] References Cited

U.S. PATENT DOCUMENTS 4,923,890  5/1990  Trainor et al. ................... 424/46

FOREIGN PATENT DOCUMENTS

0195212A2  9/1986  European Pat. Off. .
0249349A1  12/1987  European Pat. Off. .
0293029  11/1988  European Pat. Off. .
0367902  5/1990  European Pat. Off. .
0397427A1  11/1990  European Pat. Off. .
0509769A2  10/1992  European Pat. Off. .
0528633A1  2/1993  European Pat. Off. .

OTHER PUBLICATIONS

Rees et al., "Asymmetric Reduction of Dihydrofolate Using Dihydrofolate Reductase and Chiral Boron-containing Compounds," *Tetrahedron*, vol. 42, No. 1, pp. 117–136, 1986.

Frick et al., "C-NMR.-Spektren von 7,8-Dihydro-und 5,6,7,8-Tetrahydrofolsäure," *Helvetica Chimica Acta*, vol. 57, Fasc. 8, No. 293, 1974.,

*Primary Examiner*—Yogendra N. Gupta
*Attorney, Agent, or Firm*—Monte R. Browder; Robert J. Harris; Thomas E. Jackson

[57] ABSTRACT

The present invention relates to certain novel substituted ketones which are 1-pyrimidinylacetamide derivatives of formula I, set out herein, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. The invention also includes intermediates useful in the synthesis of these substituted ketones processes for preparing the substituted ketones pharmaceutical compositions containing such substituted ketones and methods for their use.

11 Claims, No Drawings

1-PYRIMIDINYLACETAMIDE HUMAN LEUKOCYTE ELASTATE INHIBITORS

The present invention relates to certain substituted ketones, in particular, certain 1-pyrimidinylacetamide compounds, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. For example, HLE has been implicated in the pathogenesis of acute respiratory distress syndrome (ARDS), rheumatoid arthritis, atherosclerosis, pulmonary emphysema, and other inflammatory disorders, including airway inflammatory diseases characterized by increased and abnormal airway secretion such as chronic bronchitis and cystic fibrosis. Also, HLE has been implicated in certain vascular diseases and related conditions (and their therapy) in which neutrophil participation is involved or implicated, for example, in hemorrhage associated with acute non-lymphocytic leukemia, as well as in raperfusion injury associated with, for example, myocardial ischaemia and related conditions associated with coronary artery disease such as angina and infarction, cerebrovascular ischaemia such as transient ischaemic attack and stroke, peripheral occlusive vascular disease such as intermittent claudication and critical limb ischaemia, venous insufficiency such as venous hypertension, varicose veins and venous ulceration, as well as impaired raperfusion states such as those associated with reconstructive vascular surgery, thrombolysis and angioplasty. The invention also includes intermediates useful in the synthesis of these substituted ketones, processes for preparing the substituted ketones, pharmaceutical compositions containing such substituted ketones and methods for their use.

In U.S. Pat. Nos. 4,880,780, of 14 Nov. 1989, and 4,910,190, of 20 Mar. 1990, assigned to ICI Americas Inc. (now ZENECA Inc.), there are disclosed two series of peptidic fluoroalkyl ketone derivatives which are HLE inhibitors. Disclosed herein is a series of substituted 2-(6-oxo-1,6-dihydro-1-pyrimidinyl)-N-[3,3-difluoro-1-(lower alkyl)-2-oxo-3-(N-substituted carbamoyl)propyl]acetamide derivatives, which unexpectedly possess inhibitory properties against HLE, which provides the basis for the present invention.

According to the invention there is provided a Compound of the invention which is a compound of formula I (formula set out, together with other formulae referred to by Roman numerals, following the Examples) wherein:

$R^0$ is (1–5C)alkyl;

R is hydrogen; or

R is an acyl group of formula A.X.CO- in which
  A.X-, taken together, is hydrogen, trifluoromethyl, 2,2,2-trifluoroethoxy, amino, methoxyamino, 2,2,2-trifluoroethylamino, RbRcN.O-, RaOCONH-, $R^1SO_2NH$-, RaOCO-, RbRcNCO- or RaCO-; or R is an acyl group of formula A.X.CJ- in which
  J is oxygen or sulfur;
  X is a direct bond, imino, oxy or thio; and
  A is as defined below or
  A is tetrahydropyran-4-yl, 1-methylpiperid-4-yl, or 5-methyl-1,3-dioxacyclohex-5-ylmethyl; or R is a sulfonyl group of formula $D.W.SO_2$- in which
  D.W-, taken together, is hydroxy, amino, di(lower alkyl)amino, 2,2,2-trifluoroethylamino, 2,2,2-trifluoroethyl, 3,3,3-trifluoropropyl or trifluoromethyl; or W is a direct bond, imino, carbonylimino, oxycarbonylimino or iminocarbonylimino; and D is as defined below; or R is a group G as defined below;

The group A, D or G is (1–6C)alkyl, (3–6C)cycloalkyl, (3–6C)cycloalkyl-(1–3C)alkyl, aryl, aryl(1–3C)alkyl, heteroaryl or heteroaryl(1–3C)-alkyl wherein an aryl or heteroaryl moiety may bear one or more halogeno, nitro, methyl or trifluoromethyl groups and further wherein the group A, D or G may bear one or more substituents selected from a group consisting of hydroxy, lower alkoxy, lower acyloxy, COORa, $CH_2COORa$, CONRbRc, $CH_2CONRbRc$, $COO(CH_2)_2NReRf$, cyano, $SO_2R^1$, $CONRdSO_2R^1$, NReRf, NRgCHO, $NRgCOR^2$, $NRgCOOR^2$, NRhCQNRiRj, $NRkSO_2R^3$, $SO_2NRlRm$, $SO_2NRnCOR^4$ and $P(O)(ORa)_2$ in which Q is oxygen or sulfur;

Ra-Rn are independently hydrogen, benzyl or lower alkyl; or, independently, a group NRbRc, NReRf, NRiRj or NRlRm is a cyclic radical selected from a group consisting of 1-pyrrolidinyl, piperidino, morpholino or 1-piperazinyl which may bear a lower alkyl substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^1$–$R^4$ are independently trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl;

$R^6$ is (1–5C)alkyl which has no tertiary carbon, (3–7C)cycloalkyl, aryl or heteroaryl, which aryl or heteroaryl independently may bear one or more of the substituents defined for the group A or an aryl or heteroaryl moiety thereof;

$R^4$ is hydrogen, (1–6C)alkyl, (3–6C)cycloalkyl, (3–6C)cycloakyl(1–3C)alkyl, aryl(1–3C)alkyl, or heteroaryl(1–3C)alkyl, wherein an aryl or heteroaryl may bear one or more halogeno, methyl or trifluoromethyl group and further wherein the group $R^4$ may bear one or more substituents selected from a group consisting of hydroxy, lower alkoxy, COORs, CONRtRu, $SO_2Rv$, $CONHSO_2Rv$, NRtRu, NRsCHO, NRsCORv, NRsCOORv, NRsCONRtRu, $NRsSO_2Rv$, $SO_2NRtRu$, $SO_2NRsCORv$, and $P(O)(ORv)_2$ in which Rs-Ru are independently hydrogen, benzyl or lower alkyl, or, independently, a group NRtRu is a cyclic radical selected from a group consisting of 1-pyrrolidinyl, piperidino, morpholino or 1-piperazinyl which may bear a lower alkyl group at the 4-position; and Rv is trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl; and provided that no aliphatic carbon is bonded to more than one nitrogen or oxygen, except as part of a cyclic ketal or where the nitrogen bears a carbonyl group; or, for a compound of formula I which is acidic or basic, a pharmaceutically acceptable salt thereof.

In this specification, the following definitions are used, unless otherwise described: Halogeno is fluoro, chloro, bromo or iodo. Alkyl, alkoxy, etc. denote both straight and branched groups; but reference to an individual radical such "propyl" embraces only the straight chain ("normal") radical, a branched chain isomer such as "isopropyl" being specifically referred to. Lower alkyl and lower alkoxy refer to radicals containing one to about four carbon atoms. Lower acyloxy refers to a radical containing one to about five carbon atoms. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms selected from the group consisting of oxygen, sulfur and nitrogen, as well as a radical of an ortho-fused bicyclic heterocycle of about eight to ten ring atoms derived therefrom, particularly a benz-derivative or one derived by fusing a propenylene, trimethylene or tetramethylene diradical thereto, as well as a stable N-oxide thereof.

It will be appreciated that, owing to the asymmetrically substituted carbon atom at the chiral center indicated by "*" in formula I, a compound of formula I may exist in, and be isolated in, optically active and racemic forms. If a compound of formula I contains an additional chiral element, such compound of formula I may exist in, and be isolated in, the form of a diastereomeric mixture or as a single diastereomer. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer. When $R^0$ is isopropyl, a compound of formula I may be viewed as a valyl derivative. In general, a compound of formula I having the (S)-configuration at the chiral center indicated by "*", which corresponds to the L-alanyl configuration, is preferred. Accordingly, it may be preferred to use the compound of formula I in a form which is characterized as containing, for example, at least 95%, 98% or 99% enantiomeric excess (ee) of the (S)-form. However, owing to the interconvertability of the (S)-isomer and the (R)-isomer by the epimerization of the chiral center indicated by "*" in formula I, it may be preferred to utilize a compound of formula I as a mixture of the (S)- and (R)-isomers at the center indicated by "*" in formula I.

As will be appreciated by those skilled in the art, a ketone of formula I can exist as a solvate, particularly a hydrate; and such a solvate of a compound of formula I is encompassed by the present invention.

A compound of formula I may exhibit polymorphism. The compound may form solvates in addition to a ketone solvate mentioned above. A compound may exist in more than one tautomeric form. It is to be understood, therefore, that the present invention encompasses any racemic or optically-active form, any polymorphic form, any tautomer or any solvate, or any mixture thereof, which form possesses inhibitory properties against HLE, it being well known in the art how to prepare optically active forms (for example, by resolution of the racemic form or by synthesis from optically-active starting materials) and how to determine the inhibitory properties against HLE by the standard tests described hereinafter.

It is preferred that the radicals $R^A$, $R^0$, R and $R^6$ not contain nor introduce an additional element of chirality into the molecule beyond the chiral center indicated by "*" in formula I.

Particular values are listed below for radicals, substituents and ranges for illustration only and they do not exclude other defined values or other values within defined ranges for the radicals and substituents.

A particular value for $R^0$ is methyl, ethyl, propyl, isopropyl or isobutyl.

A particular value for W is a direct bond or imino.

A particular value for G is (1–3C)alkyl, aryl(1–C)alkyl or heteroaryl(1–2C)alkyl which may bear one or more substituents as defined above for G or a part thereof.

A particular value of (1–6C)alkyl is methyl, ethyl, propyl, isopropyl, butyl, isobutyl, t-butyl, pentyl, 3-methylbutyl, 1-ethylpropyl, hexyl or 4-methylpentyl. A particular value of (3–6C)cycloalkyl is cyclopropyl, cyclopentyl or cyclohexyl. A particular value for the (1–3C)alkyl portion of (3–6C)cycloalkyl(1–3C)alkyl, aryl(1–3C)alkyl or heteroaryl(1–3C)alkyl is methylene, ethylene or trimethylene. A particular value for aryl is phenyl, indenyl or naphthyl. A particular value for heteroaryl is furyl, imidazolyl, tetrazolyl, pyridyl (or its N-oxide), thienyl, pyrimidinyl (or its N-oxide), indolyl or quinolinyl (or its N-oxide). A particular value for lower alkyl is methyl, ethyl, propyl, isopropyl, butyl, isobutyl or t-butyl. A particular value for lower acyloxy is acetoxy. A particular value for lower alkoxy is methoxy, ethoxy, propoxy, isoproxy or t-butoxy. A particular value for halogeno is bromo, chloro or fluoro.

A particular value for COORa is carboxy or methoxycarbonyl. A particular value for CONRbRc is carbamoyl or N,N-dimethylcarbamoyl. A particular value for NRgCOR2 is trifluoroacetylamino. A particular value of CONRdSO2R1 is N-phenylsulfonylcarbamoyl or N-(4-chlorophenylsulfonyl)carbamoyl. A particular value for A.X-, taken together, is tris(hydroxymethyl)methylamino, tris(acetoxymethyl)methylamino or 2,2-bis(hydroxymethyl)propoxy.

A particular value for $R^6$ is, for example, isopropyl, cyclopentyl, cyclohexyl, phenyl, furyl, thienyl or pyridyl in which a phenyl or heteroaryl may bear one or two substitutes as defined above.

A more particular value for $R^0$ is isopropyl. A more particular value for J is oxygen. A more particular value for X is a direct bond, imino or oxy. A more particular value for A is methyl, ethyl, phenyl, benzyl, phenethyl, pyridyl, thienyl, 5-tetrazolyl, thiazolyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group A may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for D is methyl, ethyl, isopropyl, tert-butyl, cyclohexyl, phenyl, benzyl, phenethyl, pyridyl, thienyl, 5-tetrazolyl, thiazolyl, quinolinyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group D may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, N-(4-chlorophenylsulfonyl)carbamoyl, methylsulfonylamino, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for G is methyl, ethyl, benzyl, phenethyl, pyridyl, pyridylmethyl, thenyl, 5-tetrazolylmethyl, or 2-(pyridyl)ethyl, wherein an alkyl carbon may bear an oxo group and wherein the phenyl or heteroaryl group may bear one or two halogeno or methyl groups and further wherein the group G may bear a substituent selected from hydroxy, methoxy, acetoxy, carboxy, methoxycarbonyl, ethoxycarbonyl, carbamoyl, dimethylcarbamoyl, phenylcarbamoyl, pyridylcarbamoyl, methylsulfonylamino, amino, dimethylamino, acetylamino, nicotinoylamino, or trifluoroacetylamino.

A particular value for R is, for example, hydrogen, trifluoroacetyl, hydroxyoxalyl, methoxycarbonyl, ethoxycarbonyl, isopropoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl, 2-dimethylaminoethoxycarbonyl, acetyl, carbamoylmethylaminocarbonyl, 4-(N-phenylsulfonylcarbamoyl)phenylacetyl, sulfo, aminosulfonyl, dimethylaminosulfonyl, trifluoromethylsulfonyl, methylsulfonyl (which may bear a methoxycarbonyl, carboxy or ethylsulfonyl substituent), methylaminosulfonyl, isopropylaminosulfonyl, butylsulfonyl, butylaminosulfonyl, tert-butylaminosulfonyl, cyclohexylaminosulfonyl, phenylsulfonyl (in which the phenyl may bear a chloro, nitro, amino, acetylamino, trifluoroacetylamino, methoxy, carboxy, N-(4-chlorophenylsulfonyl)carbamoyl, or methylsulfonylamino substituent at the 3- or 4-position), anilino, pyridylsulfonyl, quinolinylsulfonyl, benzylsulfonyl (in which the phenyl ring may bear a nitro or amino substituent at the 3- or 4-position), pyridylmethylsulfonyl, 2-(pyridyl)ethylsulfonyl, benzylaminosulfonyl, methyl, ethyl, benzyl, phenethyl or pyridylmethyl.

A particular value for $R^4$ is, for example hydrogen, methyl, ethyl, propyl, 2-(3-6C)cycloalkylethyl, phenethyl, 2-(pyridyl)ethyl, (wherein the phenyl or pyridyl group may bear one or two halogeno or methyl groups and further wherein the group $R^4$ may bear a substituent selected from hydroxy, methoxy, carboxy, methoxycarbonyl, ethoxycarbonyl, carbamoyl, methylsulfonyl, N-methsulfonylcarbamoyl, N-phenylsulfonylcarbamoyl, amino, and dimethylamino) or 2-(dimethylamino)ethyl, 2-morpholinoethyl, 2-piperidinoethyl or 2-(4-methylpiperazin-1-yl)ethyl.

A particular group of compounds of formula I is one in which $R^4$, $R^0$ and R have any of the values defined above and $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents; and, more particularly, $R^6$ is phenyl, 4-fluorophenyl or 2-thienyl.

Specific compounds of formula I are described in the accompanying Examples. Of these, compounds of particular interest, along with their pharmaceutically acceptable salts, include those described in Examples 2, 5, 6 and 11.

A pharmaceutically acceptable salt of an acidic compound of formula I is one made with a base which affords a pharmaceutically acceptable cation, which includes alkalai metal salts (especially lithium, sodium and potassium), alkaline earth metal salts (especially calcium and magnesium), aluminum salts and ammonium salts, as well as salts made from appropriate organic bases such as triethylamine, morpholine, piperidine and triethanol amine. A pharmaceutically acceptable salt of a basic compound of formula I includes an acid-addition salt made with an acid which provides a pharmaceutically acceptable anion, including for example, a strong acid such as hydrochloric, sulfuric or phosphoric acid.

A compound of formula I may be made by processes which include processes known in the chemical art for the production of structurally analogous heterocyclic and peptidic compounds. Such processes and intermediates for the manufacture of a compound of formula I as defined above are provided as further features of the invention and are illustrated by the following procedures in which the meanings of generic radicals are as defined above:

(A) Oxidizing a corresponding alcohol of formula II. If R is hydrogen or a group G, it will be recognized that protection of the pyridone 3-amino substituent prior to oxidation and removal of the protecting group after oxidation may be preferred or required if the amino group is not stable to the oxidation conditions employed. A convenient method is the use of excess dimethyl sulfoxide and a water soluble carbodimide, with dichloroacetic acid as a catalyst, in a inert solvent such as toluene at about room temperature, for example as described in Example 1. Other methods which may be useful include the use of alkaline aqueous potassium permanganate solution; the use of oxalyl chloride, dimethyl sulfoxide and a tertiary amine; the use of acetic anhydride and dimethyl sulfoxide; the use of chromium trioxide pyridine complex in methylene chloride; and the use of a hypervalent iodine reagent, such as a periodinane, for example 1,1,1-triacetoxy-2,1-benzoxidol-3(3H)-one with trifluoroacetic acid in dichloromethane.

(B) For a compound of formula I which contains an N-H residue, removal by using a conventional method of the nitrogen protecting group of a corresponding compound bearing a conventional nitrogen protecting group to afford the compound of formula I which contains an amino N-H residue, particularly for a compound of formula I in which R is hydrogen, removal of a group from a corresponding compound of formula I, or for a compound of formula I in which R has a value of G, the removal of an activating/protecting group Rx from a corresponding compound of formula Vb. Rx is a group which protects and activates a primary amino group for substitution, such as for example benzyloxycarbonyl or trifluoroacetyl. Conventional methods include, for example, removal of a benzyloxycarbonyl group by hydrogenolysis, as described in Example 8, part a, for an alcohol of formula II; removal of a benzyloxycarbonyl by treatment with a strong acid, as described in Example 5, for example with trifluoromethanesulfonic acid in an inert solvent such as dichloromethane; and basic hydrolysis of a trifluoroacetyl group.

(C) For a compound of formula I wherein R is an acyl group, acylation of a corresponding amine of formula I wherein R is hydrogen. Convenient methods include those described below for acylation of an amine of formula XIII, for example, when J is oxygen, the use of an activated carboxylic acid derivative, such as an acid halide, the use of a carboxylic acid and a coupling reagent, the use of an isocyanate for a compound wherein X is imino, and the use of a diactivated carbonic acid derivative, for example, carbonyldiimidazole, phosgene, diphosgene (trichloromethyl chloroformate) or triphosgene (bis(trichloromethyl) carbonate) with an alcohol of formula A.OH, a thiol of formula A.SH or an amine of formula A.NH$_2$ and a base, such as triethylamine or, when J is sulfur, the use of an activated thiocarboxylic acid derivative, such as a thioyl chloride or a lower alkyl ester of a dithioic acid, the use of a thioic acid and a coupling reagent, the use of an isothiocyanate for a compound wherein X is imino, and the use of a diactivated thiocarbonic acid derivative, for example, dimethyl trithiocarbonate, with an alcohol of formula A.OH, a thiol of formula A.SH or an amine of formula A.NH$_2$. In addition, for a compound of formula I in which R is an acyl group of formula A.X.CO- and X is oxy or imino, the acylation may be carried out by converting the corresponding amine of formula I in which R is hydrogen into its corresponding isocyanate, followed by reaction of the isocyanate with an alcohol of formula A.OH or an amine of formula A.NH$_2$, respectively, using a method similar to that described for Example 7.

(D) For a compound of formula I wherein R is a sulfonyl group, sulfonylation of a corresponding amine of formula I wherein R is hydrogen with a corresponding sulfonic acid of formula D.W.SO$_2$.OH, or an activated derivative thereof, such as an acid halide, particularly a sulfonyl (or sulfamoyl) chloride of formula D.W.SO$_2$.Cl. The sulfonylation is conveniently carried out in an inert solvent or diluent, such as dichloromethane, tetrahydrofuran or toluene, at about ambient temperature, using an organic base such as, for example, triethylamine or pyridine, or an inorganic base, such as sodium or potassium carbonate, as an acid acceptor. If a sulfonyl chloride is not commercially available, it may be obtained by a conventional method.

(E) For a compound of formula I in which R is a group G, substitution of the group L of a corresponding compound of formula G-L, wherein L is a conventional leaving group, such as for example halogeno, methylsulfonyloxy, trifluoromethylsulfonyloxy or diazonium, with a corresponding amine of formula I wherein R is hydrogen, optionally using a conventional catalyst.

(F) For a compound of formula I which bears a hydroxy substituent on an aryl or heteroaryl group, cleaving the alkyl ether or acyloxy ester of a corresponding compound of formula I which bears a lower alkoxy or lower acyloxy substituent on an aryl or heteroaryl group. Convenient methods include, for example, the cleavage of a methoxy group using boron tribromide or pyridinium chloride and the cleavage of a t-butoxy group using trifluoroacetic acid for an alkyl ether, and the acidic or alkaline hydrolysis of an acyloxy group.

(G) For a compound of formula I which bears a group of formula COORa or COORs in which Ra or Rs is hydrogen (a carboxy group), decomposing the ester group of a corresponding ester made with a conveniently removed acid protecting group, for example a corresponding compound of formula I in which Ra or Rs is not hydrogen. The decomposition may be carried out using any one of the variety of procedures well known in organic chemistry, for example basic hydrolysis using lithium or sodium hydroxide, or by hydrogenolysis of a benzyl ester.

(H) For a compound of formula I bearing a moiety of formula COORa, CH$_2$COORa, CONRbRc, CH$_2$CONRbRc, COO(CH$_2$)$_2$NReRf or CONRdSO$_2$R$^1$, acylation of a corresponding compound of formula HORa, HNRbRc, HO(CH$_2$)$_2$NReRf or HNRdSO$_2$R$^1$ with a corresponding acid of formula I bearing a moiety of formula COORa in which Ra is hydrogen, or an activated derivative thereof; or, correspondingly, for a compound of formula I bearing a moiety of formula COORs, CONRtRu or CONHSO$_2$Rv, acylation of a corresponding compound of formula HORs, HNRtRu or H$_2$NSO$_2$Rv with a corresponding acid of formula I bearing a moiety of formula COORs in which Rs is hydrogen, or an activated derivative thereof.

(I) For a compound of formula I bearing a lower acyloxy group or a group of formula NRgCHO, NRgCOR$^2$, NRgCOOR$^2$, NRhCQNRiRj or NRkSO$_2$R$^3$, acylation or sulfonylation of a corresponding compound of formula I bearing a hydroxy group or an amino group of formula NHRg, NHRh or NHRk (i.e. an amino group of formula NReRf is which Re is hydrogen and Rf is Rg, Rh or Rk) with an activated derivative of a corresponding acid of formula HOCHO, HOCOR$^2$, HOCOOR$^2$, HOCQNRiRj (including an isocyanate or isothiocyanate) or HOSO$_2$R$^3$, respectively, using a conventional method; or, correspondingly, for a compound of formula I bearing a group of formula NRsCORv, NRsCOORv, NRsCONRtRu or NRsSO$_2$Rv, acylation or sulfonylation of a corresponding compound of formula I bearing an amino group of formula NRtRu in which Rt has a value defined for Rs and Ru is hydrogen with an activated derivative of a corresponding acid of formula HOCORv, HOCOORv, HOCONRtRu (including an isocyanate) or HOSO$_2$Rv, respectively using a conventional method.

(J) For a compound of formula I which bears a heteroaryl N-oxide group, oxidation of a corresponding compound of formula I which bears a heteroaryl group using a conventional oxidant, such as for example dioxirane in acetone.

(K) For a compound of formula I which bears a primary amino group, reduction of a corresponding compound bearing a nitro group using a conventional reducing method, such as for example, hydrogenation over a palladium catalyst, or reduction with tin(II) chloride.

Whereafter, for any of the above procedures, when a pharmaceutically acceptable salt of an acidic or basic compound of formula I is required, it may be obtained by reacting the acidic or basic form of such a compound of formula I with a base or acid affording a physiologically acceptable counterion or by any other conventional procedure.

If not commercially available, the necessary starting materials for the above procedures may be made by procedures which are selected from standard techniques of heterocyclic chemistry and peptide chemistry, techniques which are analogous to the synthesis of known, structurally similar compounds, and techniques which are analogous to the above described procedures or the procedures described in the Examples. For uniformity and clarity, compounds herein are represented as the 6-pyrimidone, rather than the 6-hydroxypyrimidine, tautomers.

As will be clear to one skilled in the art, a variety of sequences is available for preparation of the starting materials. According to one of the available routes, a key intermediate pyrimidin-6-one-1-acetic acid of formula III may be prepared as shown in Scheme I (set out, together with other Schemes, following Examples) and as described in the Examples. In the Schemes, CBZ represents a benzyloxycarbonyl group.

In general, a nitrile of formula $R^6CN$ is converted into a corresponding imidic ester of formula IV wherein $R^7$ is methyl or ethyl, conveniently isolated as its hydrochloride, if the imidic ester is not commercially available. Reaction of the imidic ester with an amine of formula $H_2NCH_2R^8$ in which $R^8$ is a latent or protected carboxaldehyde group, such as vinyl, dimethoxymethyl or diethoxymethyl, affords a corresponding amidine of formula V, conveniently isolated as its hydrochloride salt. Cyclization of an amidine of formula V with diethyl ethoxymethylenemalonate affords a corresponding ethyl 1,2-disubstitied-6-pyrimidone-5-carboxylate of formula VI which is hydrolyzed to the 1,2-disubstituted-6-pyrimidone-5-carboxylic acid of formula VII.

An acid of formula VII may be converted into a corresponding isocyanate of formula VIII by a conventional method, for example by using diphenylphosphoryl azide in an inert solvent, as described in the examples. Conveniently, the isocyanate is not isolated, but is converted into a benzyl urethane of formula IX as also is shown in Scheme I. It will be clear to one skilled in the art that, in general, treatment of an isocyanate of formula VIII with a selected alcohol or amine of formula A.X.H in which X is oxy or imino will provide a corresponding product of formula IXa in which X is oxy or imino, and that the product of formula IXa may be carried forward to a corresponding product of formula I using one of the routes outlined below.

Transformation of $R^8$ into a carboxaldehyde to afford a corresponding compound of formula X from a compound of formula IX is the next step. If $R^8$ is a vinyl group, the transformation may be carried out using N-methylmorpholine-N-oxide and osmium tetroxide, as described in Example 1, part h. If $R^8$ is a dimethoxymethyl or diethoxyethyl group, the acetal may be hydrolyzed with dilute hydrochloric acid. Oxidation of an acetaldehyde derivative of formula X to provide a corresponding substituted acetic acid of formula III is conveniently carried out as described in Example 1f using sodium chlorite as the oxidant.

The intermediate amines of formulae A, B and C, may be prepared as outlined in Scheme Ia using known or analogous methodology. For example, the preparation of the common intermediate of formula D wherein $R^0$ is isopropyl from L-valinol is described in Example 1 of U.S. Pat. No. 4,880,780, as is the corresponding compound of formula E in which $R^4$ is benzyl. Preparations of the intermediate of formula D wherein $R^0$ is isopropyl and corresponding intermediates of formulae E and B (for example with $R^4$ as propyl or phenethyl) are also described in European Patent Application, Publication No. 397,427 A1, inter alia. The hydroxy group of a compound of formula E may be protected by a conventional method to afford a corresponding compound of formula F, wherein Rp represents an alcohol protecting group, conveniently tert-butyldimethylsilyl. Removal of the amine protecting group of a compound of formula D, E or F by a conventional method, for example as described in Example 1, part a, affords a corresponding amine of formula A, B or C, which may be conveniently isolated and used as its acid addition salt, for example the hydrochloride or hydrobromide salt. As outlined in Scheme II, an acid of formula III may be coupled with an amine of formula A, B or C, for example as described in Example 1, part b, to afford a corresponding product of formula XVIIIc, XVIIIa or XVIII, respectively. Treatment of an ester of formula XVIIIc with an amine of formula $R^4NH_2$, for example as described in Example 1, part c, affords a corresponding amine of formula XVIIIa. By using a conventional method, the hydroxy group of a compound of formula XVIIIa may be protected to afford a corresponding compound of formula XVIII. (Conversely, a compound of formula XVIII may be deprotected to afford a compound of formula XVIIIa.)

The benzyloxycarbonyl group of a compound of formula XVIII may be removed by a conventional method, for example by hydrogenolysis, to afford a corresponding 3-amino pyridone of formula XIX. A 3-amino pyridone of formula XIX may then be acylated, sulfonylated or be substituted with a group G by using a conventional method to afford a corresponding pyridone of formula XX. Conventional acylation and sulfonylation methods and methods for introducing a group G include those described above in processes (C), (D) and (E) for substituting an amine of formula I wherein R is hydrogen. (Should a portion of bis-sulfonylated product be obtained, treatment with aqueous base at an elevated temperature may be used to remove the more labile second sulfonyl group at a convenient stage in the synthesis.) Removal of a tert-butyldimethylsilyl group to provide a corresponding alcohol of formula II may be carried out using tetrabutylammonium fluoride in an inert solvent; it may be preferred to use acetic acid to buffer the reaction conditions. An alternative order of steps can be used as well. Thus, removal of the alcohol protecting group of a compound of formula XVIII affords the corresponding alcohol of formula XVIIIa. Deprotection of the amino group of a compound of formula XVIIIa affords a corresponding amino ketone of formula II wherein R is hydrogen which may be converted into a corresponding compound of formula II using a conventional procedure as described above for conversion of a compound of formula XIX into a compound of formula XX.

Alternatively, for preparation of an intermediate of formula Vb, oxidation of an alcohol of formula XVIIIa, which is an alcohol of formula II wherein R is benzyloxycarbonyl, using a method described in process (A), affords a corresponding ketone of formula I wherein R is benzyloxycarbonyl. Removal of the nitrogen protecting group of a ketone of formula I wherein R is benzyloxycarbonyl by hydrogenolysis or by treatment with a strong acid, for example as described in Example 5, affords a corresponding amine of formula I wherein R is hydrogen. A preferred method for introducing the substituent R when it is a group G, particularly when it is an alkyl or substituted alkyl group, is by the use of a corresponding compound in which the pyrimidone 5-amino substituent bears an activating/protecting group of formula Rx, for example, benzyloxycarbonyl or trifluoroacetyl. Thus, acylation of a compound of formula I wherein R is hydrogen with trifluoroacetic anhydride affords a corresponding compound of formula Va in which Rx is trifluoroacetyl, which compound also may be prepared by an alternative order of steps via the corresponding compound of formula XIX. It will be noted that each of a compound of formula Va in which Rx is benzyloxycarbonyl or trifluoroacetyl is also a compound of formula I in which R is an acyl group. Alkylation, using a corresponding reagent of formula G.L in which G is alkyl or substituted alkyl, then provides a corresponding intermediate of formula Vb.

It may be desired optionally to use a protecting group during all or portions of the above described processes; the protecting group then may be removed when the final compound or a required starting material is to be formed. As will be clear to one skilled in the art, the order of steps in the sequences leading to the starting materials and products of the invention may be altered if appropriate considerations relative to coupling methods, racemization, deprotection methods, etc. are followed.

The utility of a compound of the invention or a pharmaceutically acceptable salt thereof (hereinafter, collectively referred to as a "Compound") may be demonstrated by standard tests and clinical studies, including those described below.

Inhibition Measurements:

The potency of a Compound to act as an inhibitor of human leukocyte elastase (HLE) on the low molecular weight peptide substrate methoxy-succinyl-alanyl-alanyl-prolyl-valine-p-nitroanilide is determined as described in U.S. Pat. No. 4,910,190. The potency of an inhibitor is evaluated by obtaining a kinetic determination of the dissociation constant, $K_i$, of the complex formed from the interaction of the inhibitor with HLE. If a Compound is found to be a "slow-binding" inhibitor of HLE, special methods of analysis to accurately determine $K_i$ values for the inhibition of HLE are carried out as described in U.S. Pat. No. 4,910,190. In general, the $K_i$ values for Compounds of the invention which were tested are generally on the order of $10^{-7}$M or much less.

Acute Lung Injury Model:

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model (described in Williams et al., *American Review of Respiratory Disease* (1991), 144, 875–883) was used.

Hamsters are first lightly anesthetized with Brevital. Phosphate buffered saline (PBS) pH 7.4, either alone or containing human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them intratracheally as solutions or suspensions in PBS, either with or at various times prior to the HLE challenge (400 $\mu$g), or by dosing them intravenously or orally as solutions at various times prior to the HLE challenge (100 $\mu$g) to determine their utility in preventing an HLE lesion. A solution of a Compound is conveniently prepared using 10% polyethylene glycol 400/PBS or 10% polyethylene glycol 400/water. For a Compound which is acidic or basic, base (e.g. sodium hydroxide solution) or acid (e.g. hydrochloric acid) may be added as indicated to achieve solution. Compounds of this invention produced statistically significant reductions in wet lung weight and total lavagable cells relative to HLE alone.

Acute Hemorrhagic Assay:

This assay relies on monitoring only the amount of hemorrhage in the lung following intratracheal administration of human neutrophil elastase (HNE). Hemorrhage is quantified by disrupting erythrocytes recovered in lung lavage fluid and comparing that to dilutions of whole hamster blood. The screening protocol, similar to that described in Fletcher et al., *American Review of Respiratory Disease* (1990), 141, 672–677, is as follows. Compounds demonstrated to be HNE inhibitors in vitro are conveniently prepared for dosing as described above for the Acute Lung Injury Model. The compounds are then dosed by mouth to male Syrian hamsters at a fixed time, such as 30 or 90 min, prior to intratracheal administration of 50 $\mu$g/animal of HNE in 300 $\mu$L phosphate buffered saline (PBS) pH 7.4. Four hours after enzyme administration, the animals are killed with an overdose of pentobarbital sodium, the thorax opened and the lungs and trachea removed. The excised lungs are lavagad with three changes of 2 mL normal saline via a tracheal cannula. The recovered lavagas are pooled, the volumes (about 5 mL) are recorded and the lavages stored at 4° C. until assayed. For calculation of the amount of blood in each sample, the thawed lavages and a sample of whole hamster blood are sonicated to disrupt erythrocytes and appropriately diluted into individual wells of a 96-well microtiter plate. The optical densities (OD) of the disrupted lavages and blood samples are determined at 405 nm. The ($\mu$L blood equivalents)/(mL lavage) are determined by comparing the OD of the test samples with the OD of the standard curve prepared from whole hamster blood. The total $\mu$L equivalents of blood recovered is determined by multiplying recovered lavage volume by the ($\mu$L blood equivalents)/(mL lavage) for each sample. Results are reported as % inhibition of hemorrhage with respect to PBS treated controls when the test compound is given at a specified dose and time prior to administration of HNE.

No overt toxicity was observed when Compounds of the invention were administered in the above in vivo tests.

It will be appreciated that the implications of a Compound's activity in the Acute Lung Injury Model or Acute Hemorrhagic Assay are not limited to emphysema, but, rather, that the test provides evidence of general in vivo inhibition of HLE.

Compounds of the present invention which were tested exhibited activity in at least one of the tests described above under Inhibition Measurement, Acute Lung Injury Model and Acute Hemorrhagic Assay. It should be noted that, as would be expected in comparison of in vitro and in vivo results, there was not always a direct correlation between the activities of the compounds measured as $K_i$ values in the Inhibition Measurement test and the reduced values for total lavagable cells and wet lung weights relative to the administration of HLE alone obtained in the Acute Lung Injury Model test or inhibition of hemorrhage in the Acute Hemorragic Assay.

According to a further feature of the invention, there is provided a pharmaceutical composition comprising a pharmaceutically effective amount of a Compound and a pharmaceutically acceptable diluent or carrier. As noted above, another feature of the invention is a method of using a Compound of the invention in the treatment of a disease or condition in a mammal, especially a human, in which HLE is implicated.

A Compound of the present invention may be administered to a warm-blooded animal, particularly a human, in need thereof for treatment of a disease in which HLE is implicated, in the form of a conventional pharmaceutical composition, for example as generally disclosed in U.S. Pat. No. 4,910,190. The preferred mode of administration may be via a powdered or liquid aerosol. In a powdered aerosol, a Compound of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of a Compound of the invention with the remainder of the 20 mg capsule being a pharmaceutically acceptable carrier such as lactose. In aliquid aerosol, a Compound of the invention may be administered using a nebulizer such as, for example, a 'Retec' (trademark) nebulizer, in which the solution is nebulized with compressed air. The aerosol may be administered, for example, at the rate of one to about eight times per day as follows: A nebulizer is filled with a solution of a Compound, for example 3.5 mL of solution containing 10 mg/mL; the solution in the nebulizer is nebulized with compressed air; and the patient breathes normally (tidal volume) for eight minutes with the nebulizer in his mouth.

Alternatively, the mode of adminstration may be oral or parenteral, including subcutaneous deposit by means of an osmotic pump. A compound of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 mL intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

For parenteral administration or use in an aerosol, a 10 mg/mL aqueous formulation of an acidic Compound may be prepared, for example by dissolving the Compound (10 mg), dibasic sodium phosphate heptahydrate, USP (11.97 mg), monobasic sodium phosphate, USP (0.74 mg), sodium chloride, USP (4.50 mg) and sufficient 1N sodium hydroxide solution or 0.05M monobasic sodium phosphate solution to achieve pH 7.0–7.5 in sufficient water for injection, USP to afford 1.0 mL (1.01 g), followed by aseptic filtration, and sterile storage using standard procedures.

In general, a Compound of the invention will be administered to humans at a daily dose in the range of, for example, 5 to 100 mg of the Compound by aerosol or 50 to 1000 mg intravenously, or a combination of the two. However, it readily will be understood that it may be necessary to vary the dose of the Compound administered in accordance with well known medical practice to take account of the nature and severity of the disease under treatment, concurrent therapy, and the age, weight and sex of the patient receiving treatment. It similarly will be understood that generally equivalent amounts of a pharmaceutically acceptable salt of the Compound also may be used. Protocols for the administration of an HLE inhibitor and evaluation of the patients are described in the European Patent Applications with Publication Numbers 458535, 458536, 458537, and 463811 for the treatment or prevention of cystic fibrosis, ARDS, bronchitis, and hemorrhage associated with acute non-lymphocytic leukemia or its therapy, respectively; and a Compound of the invention may be used similarly for the treatment of those diseases and conditions either alone or in combination with another therapeutic agent customarily indicated for the treatment of the particular condition. For therapeutic or prophylactic treatment of a vascular disease or related condition in a mammal in which neutrophils are involved or implicated, a Compound of the invention may conveniently be administered by a parenteral route, either alone or simultaneously or sequentially with other therapeutically active agents customarily administered for the condition.

The invention will now be illustrated by the following non-limiting examples in which, unless stated otherwise:

(i) temperatures are given in degrees Celsius operations were carried out at room or ambient temperature, that is, at a temperature in the range of 18°–25° C.;

(ii) organic solutions were dried over anhydrous sodium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany); if "acidic silica gel" is indicated, material custom prepared by J. T. Baker Chemical Co., Phillipsburg, N.J., U.S.A., and having a pH of about 6 when slurried in water was used; reversed phase chromatography means flash chromatography over octadecylsilane (ODS) coated support having a particle diameter of 32–74μ, know as "PREP-40-ODS" (Art 731740-100 from Bodman Chemicals, Aston, Pa., U.S.A.); thin layer chromatography (TLC) was carried out on 0.25 mm silica gel GHLF plates (Art 21521 from Analtech, Newark, Del., U.S.A.); reversed phase-TLC (RP-TLC) was carried out Whatman MKC$_{18}$F plates (Art 4803-110 from Bodman Chemicals);

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 250 MHz using DMSO-d$_6$ as solvent; conventional abbreviations for signal shape are used; for AB spectra the directly observed shifts are reported;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionization mode using a direct exposure probe; where indicated ionization was effected by electron impact (EI) or fast atom bombardment (FAB); generally, only peaks which indicate the parent mass are reported.

EXAMPLE 1

2-(5-Benzyloxycarbonylamino-6-oxo-2-phenyl-1,6-dihydropyrimidin-1-yl)-N-[3,3-difluoro-1-isopropyl-2-oxo-3-(N-propylcarbamoyl)propyl]acetamide.

To a solution of the alcohol from Example 1.c. (0.72 g) in 1:1 dimethylsulfoxide:toluene (12 mL) was added 1-ethyl-3-(3-dimethylaminopropylcarbodiimide (2.3 g) and dichloroacetic acid (0.39 mL). The solution changed color from yellow to black. After 1 hour, the reaction was diluted with water and extracted with ethyl acetate. The extracts were washed (saturated sodium bicarbonate, brine), dried and evaporated. The crude product was purified by chromatography; three columns, with dichloromethane:methanol (gradient, 100:0, 97:3) as the eluent for the first and second, and with chloroform:methanol (gradient, 100:0, 40:1) as the eluent for the third, to give the title compound (0.331 g) as a white solid; TLC: R$_f$=0.46, methanol:dichloromethane (10:90); 300 MHz NMR: 0.74 (d,3), 0.81 (t,3), 0.85 (d,3), 1.40–1.48 (m,2), 2.19–2.25 (m,1), 3.08 (q,2), 4.54 (q,2), 4.82 (dd, 1), 5.19 (s,2), 7.33–7.53 (m,10), 8.45 (s,1), 8.60 (d,1), 8.96 (s,1), 9.10 (t,1); MS: m/z=598 (M+1). Analysis for C$_{30}$H$_{33}$F$_2$N$_5$O$_6$.0.35 H$_2$O: Calculated: C, 59.67; H, 5.62; N, 11.60; Found: C, 59.67; H, 5.54; N, 11.26.

The starting alcohol was prepared as follows.

a. Ethyl (4S)-4-amino-2,2-difluoro-3-hydroxy-5-methylhexanoate hydrobromide. To a solution of ethyl (4S)-4-benzyloxycarbonylamino-2,2-difluoro-3-hydroxy-5-methylhexanoate (30.04 g, prepared as described in European Patent Application, Publication No. 397 427 A1, Example 1f; see also, U.S. Pat. No. 4,880,780, Example 1) in glacial acetic acid (200 mL) was added a solution of 30% (w/w) hydrogen bromide in acetic acid (75 mL). The mixture was allowed to stir for 2.5 hours, and was evaporated to a paste. The residue was evaporated twice from toluene and the resulting solids were triturated with diethyl ether. The solids were washed with diethyl ether and dried under vacuum to give the hydrobromide salt (13.85 g) as a light brown powder; 300 MHz NMR (DHSO/trifluoroacetic acid): 0.96 (m,6), 1.30 (t,2, J=8.5), 2.04 (m,1), 3.20 (m,2), 4.21 (m,1), 4.35 (m,2); MS: m/z=226 (M+1).

b. 2-(5-Benzyloxycarbonylamino-6-oxo-2-phenyl-1,6-dihydropyrimidin-1-yl)-N-[3,3-difluoro-2-hydroxy-1-isopropyl-3-(ethoxycarbonyl)propyl]acetamide.

To a solution of 2-(5-benzyloxycarbonylamino-6-oxo-2-phenyl-1,6-dihydropyrimidin-1-yl)acetic acid (1.93 g), 1-hydroxybenzotriazole hydrate (1.38 g), 4-methylmorpholine (about 1.4 mL) and the hydrobromide salt from Example 1.a. (1.56 g) in tetrahydrofuran (50 mL) was added 1-(3-dimethylaminopropyl)-3-ethylcarbodiimide hydrochloride (1.12 g). The resulting solution was stirred overnight. The mixture was diluted with chloroform, washed (10% hydrochloric acid, saturated sodium bicarbonate), dried, and evaporated to give a tan foam (2.52 g). The foam was purified by chromatography, with chloroform:methanol (30:1) as the eluent, to give the amide (1.82 g) as a white solid; TLC: R$_f$=0.32, methanol:chloroform (5:95); NMR: 0.79 (d,3, J=6.6), 0.87 (d,3, J=6.6), 1.25 (t,3,), 1.70–1.80 (m,1), 3.82 (t,1, J=8.8), 4.24–4.62 (m,5), 5.19 (s,2), 6.27 (d,1, J=7.2), 7.33–7.53 (m,10), 7.90 (d,1, J=9.7), 8.45 (s,1), 8.95 (s,1); MS: m/z=587 (M+1).

c. 2-(5-Benzyloxycarbonylamino-6-oxo-2-phenyl-1,6-dihydropyrimidin-1-yl)-N-[3,3-difluoro-2-hydroxy-1-isopropyl-3-(N-propylcarbamoyl)propyl]acetamide. To a solution of the product from Example 1.b. (0.75 g) in ethanol (10 mL) was added propylamine (0.95 mL). The solution was stirred overnight, diluted with chloroform, washed, (10% hydrochloric acid, brine), dried, and evaporated to yield the alcohol (0.73 g) as an off-white solid; TLC: R$_f$=0.34, methanol:chloroform (5:95); 300 MHz NMR: 0.76 (d,3), 0.81 (t,3), 0.84 (d,3), 1.40–1.47 (m,2), 1.60–1.72 (m,1), 2.98–3.10 (m,2), 3.77 (t,1), 4.00–4.25 (m,1), 4.51 (s,2), 5.19 (s,2), 6.06 (d,1), 7.31–7.53 (m,10), 7.87 (d,1), 8.34 (t,1), 8.46 (s,1), 8.94 (s,1); MS: m/z=600 (M+1).

The intermediate 2-(5-benzyloxycarbonylamino-6-oxo-2-phenyl-1,6-dihydropyrimidin-1-yl)acetic acid used in Example 1.b. was prepared as follows:

d. N-Allylbenzamidine hydrochloride. To a solution of ethyl benzimidate hydrochloride (20 g) in methanol at 0° C. was added allyl amine. The resulting solution was allowed to stand for 2 days at 5° C. The solution was evaporated to yield a solid which was collected and washed with ether to give N-allylbenzamidine hydrochloride (21.5 g) as a white solid; 300 MHz NMR: 10.1 (s,1), 9.68 (s,1), 9.29 (s,1), 7.72 (s,5), 5.92 (m,1), 5.35 (d,2), 5.26 (d,2), 4.14 (s,2).

e. Ethyl 1-allyl-2-phenylpyrimidin-6(1H)-one-5-carboxylate. The free base of N-allylbenzamidine hydrochloride was generated by dissolving N-allylbenzamidine hydrochloride (79.7 g) in 1N sodium hydroxide. The free base was then extracted into dichloromethane, which was dried and evaporated to provide N-allylbenzamidine (65.2 g). This was added to diethyl ethoxymethylenemalonate (78 mL) in ethanol (50 mL). The resulting solution was heated at 120° C. for 2 hours. The solution was cooled, diluted with ethyl acetate, washed (saturated ammonium chloride, water), dried, and evaporated to give a solid, which was collected and washed two times with ether:hexane (1:1), to provide ethyl 1-allyl-2-phenylpyrimidin-6(1H)-one-5-carboxylate (62.5 g) as a white solid; 300 HHz NMR: 8.56 (s,1), 7.54 (m,5), 5.80 (m,1), 5.09 (d,1), 4.82 (d,1), 4.47 (d,2), 4.28 (q,2), 1.28 (t,3).

f. 1-Allyl-2-phenylpyrimidin-6(1H)-one-5-carboxylic acid. To a solution of ethyl 1-allyl-2-phenylpyrimidin-6(1H)-one-5-carboxylate (25.6 g) in tetrahydrofuran (300 mL) at 0° C. was added a solution of 0.5N sodium hydroxide (198 mL). The resulting solution was allowed to stir for 1 hour, was poured into dichloromethane and the organic layer removed. The remaining aqueous fraction was extracted with dichloromethane, acidified with 1N hydrochloric acid (pH 2), and extracted with dichloromethane. The organic extracts from the acidified extraction were dried and evaporated to give an oil which crystallized upon addition of ether. The resulting white solid was collected and washed with ether:hexane (1:1) to give 1-allyl-2-phenylpyrimidin-6(1H)-one-5-carboxylic acid (11.1 g); 300 MHz NMR: 13.0 (broad s,1), 8.69 (s,1), 7.58 (m,5), 5.82 (m,1), 5.16 (d,1), 4.87 (d,1), 4.51 (d,2).

g. 1-Allyl-5-benzyloxycarbonylamino-2-phenylpyrimid-6(1H)-one. To a solution of 1-allyl-2-phenylpyrimidin-6(1H)-one-5-carboxylic acid (30.2 g) and triethylamine (32.8 mL) in dioxane (390 mL) was added diphenylphosphoryl azide (25.6 mL), and the resulting solution was heated at 100° C. for 2 hours. Benzyl alcohol (24.5 mL) was added and the resulting solution heated at 100° C. for 12 hours. The solution was cooled and the solvent evaporated. The residue was dissolved in ethyl acetate, washed (saturated ammonium chloride, 1N sodium hydroxide, water), dried and evaporated to give an oil that crystallized upon addition of ether yielding a white solid that was collected and washed with ether to provide 1-allyl-5-benzyloxycarbonylamino-2-phenylpyrimid-6(1H)-one (25.1 g); 300 MHz NMR: 8.93 (s,1), 8.45 (s,1), 7.43 (m,10), 5.75 (m,1), 5.18 (s,2), 5.08 (d,1), 4.82 (d,1), 4.46 (d,2).

h. 5-Benzyloxycarbonylamino-6-oxo-2-phenyl-1,6-dihydro-1-pyrimidinylacetaldehyde. To a solution of 1-allyl-5-benzyloxycarbonylamino-2-phenylpyrimid-6(1H)-one in tetrahydrofuran (200 mL) and water (30 mL) was added N-methylmorpholine-N-oxide (9.82 g) and osmium tetroxide (4.4 mL, 4% in water). The resulting solution was allowed to stir overnight. N-Methylmorpholine-N-oxide (1.65 g) was added and the solution was allowed to stir for 4 hours. Sodium thiosulfate (saturated aqueous solution, 10 mL) and diatomaceous earth (30 g) were added and the mixture was stirred for 0.5 hour. The mixture was filtered and evaporated to give an oil. This oil was dissolved in ethyl acetate, washed (saturated aqueous sodium thiosulfate solution, 1N hydrochloric acid, brine), and evaporated to give an oil. The oil was dissolved in ethanol (230 mL) and a solution of sodium periodate (27 g) in water (40 mL) was added. The mixture was stirred for 2 hours, filtered through diatomaceous earth and evaporated. The residue was dissolved in ethyl acetate, washed with water, dried, and evaporated to provide 5-benzyloxycarbonylamino-6-oxo-2-phenyl-1,6-dihydro-1-pyrimidinylacetaldehyde (25 g) as a white solid; TLC: $R_f$=0.8, ethyl acetate:diethyl ether (1:1).

i. 5-Benzyloxycarbonylamino-6-oxo-2-phenyl-1,6-dihydro-1-pyrimidinylacetic acid. To a solution of 5-benzyloxycarbonylamino-6-oxo-2-phenyl-1,6-dihydro-1-pyrimidinylacetaldehyde (25 g) in tert-butyl alcohol (175 mL), and 2-methyl-2-butene (148 mL) at 0° C. was added a solution of sodium chlorite (57 g) and sodium dihydrogen phosphate monohydrate (67 g) in water (190 mL). The mixture was allowed to stir for 3 hours and was evaporated. The resulting material was diluted with ethyl acetate and extracted with 1N aqueous sodium hydroxide. The aqueous solution was acidified to pH 3 with hydrochloric acid and was extracted with dichloromethane. The organic extracts were dried and evaporated to give a white solid, which was washed with ether:hexane (1:1) to yield the acid (17.2 g); 300 MHz NMR: 13.3 (s,1), 9.04 (s,1), 8.48 (s,1), 7.43 (m,10), 5.19 (s,2), 4.51 (s,2).

EXAMPLE 2

2-(5-Benzyloxycarbonylamino-6-oxo-2-phenyl-1,6-dihydropyrimidin-1-yl)-N-[3,3-difluoro-1-isopropyl-2-oxo-3-(N-phenethylcarbamoyl)propyl]acetamide.

2-(5-Benzyloxycarbonylamino-6-oxo-2-phenyl-1,6-dihydropyrimidin-1-yl)-N-[3,3-difluoro-2-hydroxy-1-isopropyl-3-(N-phenethylcarbamoyl)propyl]acetamide was subjected to conditions similar to those described in Example 1 to give the crude ketone, which was purified by chromatography, with methanol:chloroform (gradient, 98:2, 97:3) as the eluent, to give the title compound; TLC: $R_f$=0.23 methanol:chloroform (5:95); MS: m/z=660 (M+1). Analysis for $C_{35}H_{35}F_2N_5O_6 \cdot 0.4$ $H_2O$: Calculated: C, 63.04; H, 5.41; N, 10.50; Found: C, 62.97; H, 5.37; N, 10.52.

The intermediate 2-(5-benzyloxycarbonylamino-6-oxo-2-phenyl-1,6-dihydropyrimidin-1-yl)-N-[3,3-difluoro-2-hydroxy-1-isopropyl-3-(N-phenethylcarbamoyl)propyl]acetamide was prepared as follows:

Using a procedure similar to that described in Example 1.c., substituting phenethylamine for propylamine and purifying by chromatography, with chloroform:methanol (97:3) as the eluent, the phenethylcarbamoyl compound was prepared; TLC: $R_f$=0.34, methanol:chloroform (5:95); MS: m/z=662 (M+1).

EXAMPLE 3

2-(5-Benzyloxycarbonylamino-6-oxo-2-phenyl-1,6-dihydropyrimidin-1-yl)-N-[3,3-difluoro-1-isopropyl-2- oxo-3-[N-[2-(2-pyridyl)ethyl]carbamoyl]propyl]acetamide.

2-(5-Benzyloxycarbonylamino-6-oxo-2-phenyl-1,6-dihydropyrimidin-1-yl)-N-[3,3-difluoro-2-hydroxy-1-isopropyl-3-[N-[2-(2-pyridyl)ethyl]carbamoyl]propyl]acetamide was subjected to conditions similar to those described in Example 1 to give the crude ketone, which was purified by chromatography, with dichloromethane:ethyl acetate:methanol (gradient, 60:40:0, 60:39:1, 38:60:2) as the eluent, to give the title compound; TLC: $R_f=0.65$, methanol:chloroform (5:95), then methanol:-dichloromethane (5:95); MS: m/z=661 (M+1). Analysis for $C_{34}H_{34}F_2N_6O_6$·0.5 $H_2O$: Calculated: C, 60.98; H, 5,27; N, 12.55; Found: C, 61.00; H, 5.17; N, 12.62.

The intermediate 2-(5-benzyloxycarbonylamino-6-oxo-2-phenyl-1,6-dihydropyrimidin-1-yl)-N-[3,3-difluoro-2-hydroxy-1-isopropyl-3-[N-[2-(2-pyridyl)ethyl]carbamoyl]propyl]acetamide was prepared as follows:

Using a procedure similar to that described in Example 1.c., substituting 2-(2-pyridyl)ethylamine for propylamine and an ammonium chloride wash for the 10% hydrochloric acid wash, the 2-(2-pyridyl)ethyl compound was prepared. The crude material was purified by trituration with ether; TLC: $R_f=0.23$, methanol:-chloroform (5:95); MS: m/z=663 (M+1).

EXAMPLE 4

2-(5-Benzyloxycarbonylamino-6-oxo-2-phenyl-1,6-dihydropyrimidin-1-yl)-N-[3,3-difluoro-1-isopropyl-2-oxo-3-[N-(4-pyridylmethyl)carbamoyl]propyl]acetamide.

2-(5-Benzyloxycarbonylamino-6-oxo-2-phenyl-1,6-dihydropyrimidin-1-yl)-N-[3,3-difluoro-2-hydroxy-1-isopropyl-3-[N-(4-pyridylmethyl)carbamoyl]propyl]acetamide was subjected to conditions similar to those described in Example 1 to yield the crude ketone, which was purified by chromatography, with dichloromethane:ethyl acetate:methanol (50:48:2) as the eluent. The resulting material was crystallized from methanol:-chloroform and hexanes to give the title compound; TLC: $R_f=0.28$, methanol:ethyl acetate:dichloromethane (2:48:50); MS: m/z=647 (M+1). Analysis for $C_{33}H_{32}F_2N_6O_6$·0.3 $H_2O$: Calculated: C, 60.79; H, 5.04; N, 12.89; Found: C, 60.84; H, 5.03; N, 12.87.

The intermediate 2-(5-benzyloxycarbonylamino-6-oxo-2-phenyl-1,6-dihydropyrimidin-1-yl)-N-[3,3-difluoro-2-hydroxy-1-isopropyl-3-[N-(4-pyridylmethyl)carbamoyl]propyl]acetamide was prepared as follows:

Using a procedure similar to that described in Example 1.c., substituting 4-pyridylmethylamine for propylamine, the 4-pyridylmethylcarbamoyl compound was prepared. The majority of the product precipitated from the reaction mixture and was isolated by filtration. The filtrate was then worked up as described in Example 1.c., except a saturated ammonium chloride wash was used instead of the 10% hydrochloric acid wash; TLC: $R_f=0.21$, methanol:chloroform (1:20); MS: m/z=649 (M+1).

EXAMPLE 5

2-(5-Amino-6-oxo-2-phenyl-1,6-dihydropyrimidin-1-yl)-N-[3,3-difluoro-1-isopropyl-2-oxo-3-(N-propylcarbamoyl)propyl]acetamide.

A suspension of the product from Example 1 (0.29 g) in dichloromethane (4 mL) and anisole (0.17 mL) was cooled in an ice-water bath. Trifluoromethanesulfonic acid (0.23 mL) was added to the mixture dropwise. The dark colored, gummy reaction mixture was allowed to warm to room temperature. After 30 minutes, the reaction mixture was cooled in an ice-water bath and was quenched with saturated sodium bicarbonate. The mixture was extracted with ethyl acetate and the extracts were washed (saturated sodium bicarbonate, brine), dried, and evaporated. The crude product was purified by trituration with ether to yield the title compound as a white solid (0.16 g); TLC: $R_f=0.19$, methanol:dichloromethane (5:95); NMR: 0.75 (d,3), 0.82 (t,3), 0.86 (d,3), 1.40–1.50 (m,2), 2.20–2.30 (m,1), 3.08 (q,2), 4.50 (q,2), 4.82 (dd,1), 5.17 (broad s, 2); MS: m/z=464 (M+1).

EXAMPLE 6

2-(5-Amino-6-oxo-2-phenyl-1,6-dihydropyrimidin-1-yl)-N-[3,3-difluoro-1-isopropyl-2-oxo-3-(N-phenethylcarbamoyl)propyl]acetamide.

The title product was prepared from the product of Example 2 utilizing conditions similar to those described in Example 5. The crude product was purified by chromatography, with dichloromethane:methanol (gradient, 97:3, 95:5) as the eluent, to give the title compound; TLC: $R_f=0.28$, methanol:dichloromethane (10:90); MS: m/z=526 (M+1). Analysis for $C_{27}H_{29}F_2N_5O_4$: Calculated: C, 61.71; H, 5.56; N, 13.33; Found: C, 61.48; H, 5.60; N, 13.08

EXAMPLE 7

2-(5-Amino-6-oxo-2-phenyl-1,6-dihydropyrimidin-1-yl)-N-[3,3-difluoro-1-isopropyl-2-oxo-3-[N-[2-(2-pyridyl)ethyl]carbamoyl]propyl]acetamide.

The title product was prepared from the product of Example 3 utilizing conditions similar to those described in Example 5. The crude product was purified by chromatography, with dichloromethane:methanol (gradient, 98:2, 95:5) as the eluent, to give the title compound; TLC: $R_f=0.25$, methanol:dichloromethane (5:95); MS: m/z=527 (M+1). Analysis for $C_{28}H_{28}F_2N_6O_4$·0.65 $H_2O$: Calculated: C, 58.02; H, 5.49; N, 15.61; Found: C, 57.99; H, 5.33; N, 15.54.

EXAMPLE 8

2-(5-Acetylamino-6-oxo-2-phenyl-1,6-dihydropyrimidin-1-yl)-N-[3,3-difluro-1-isopropyl-2-oxo-3-(N-propylcarbamoyl)propyl]acetamide.

2-(5-Acetylamino-6-oxo-2-phenyl-1,6-dihydropyrimidin-1-yl)-N-[3,3-difluoro-2-hydroxy-1-isopropyl-3-(N-propylcarbamoyl)propyl]acetamide was subjected to conditions similar to those described in Example 1 to provide the title compound; TLC: $R_f=0.35$, methanol:-dichloromethane (5:95); MS: m/z=506 (M+1). Analysis for $C_{24}H_{29}F_2N_5O_5$·0.5 $H_2O$: Calculated: C, 56.02; H, 5.88; N, 13.61; Found: C, 56.07; H, 5.78; N, 13.57.

The starting alcohol was prepared as follows.

a. 2-(5-Amino-6-oxo-2-phenyl-1,6-dihydropyrimidin-1-yl)-N-[3,3-difluoro-2-hydroxy-1-isopropyl-3-(N-propylcarbamoyl)propyl]acetamide. 2-(5-Benzyloxycarbonylamino-6-oxo-2-phenyl-1,6-dihydropyrimidin-1-yl)-N-[3,3-difluoro-2-hydroxy-1-isopropyl-3-(N-propylcarbamoyl)propyl]acetamide (0.7 g) was dissolved in ethanol (15 mL) with heating. To the solution was added 10% (w/w) palladium on carbon (0.7 g) and the mixture was shaken under a hydrogen atmosphere (3 bar) overnight. The mixture was filtered through diatomaceous earth and concentrated. The residue was once again subjected to the above hydrogenation conditions. After 4.5 hours, the mixture was filtered through diatomaceous earth and the filtrate concentrated to a glassy film. The residue was redisolved and evaporated from dichloromethane/hexane, ether/hexane and hexane to yield the product as a solid (0.54 g); TLC: $R_f=0.38$, methanol:dichloromethane (5:95); NMR: 0.78 (d,2), 0.82 (t,3), 0.86 (d,3), 1.40–1.50 (m,2), 1.60–1.75 (m,1), 2.90–3.10 (m,2), 3.77 (t,1), 4.00–4.20 (m,1), 4.46 (broad s, 2), 5.16 (broad s, 2), 6.05 (d,1), 7.34 (s,1), 7.37–7.47 (m,5), 7.78 (d,1), 8.36 (t,1); MS: m/z=466 (M+1).

b. 2-(5-Acetylamino-6-oxo-2-phenyl-1,6-dihydropyrimidin-1-yl)-N-[3,3-difluoro-2-hydroxy-1-isopropyl-3-(N-propylcarbamoyl)propyl]acetamide. To a solution of the product from Example 8.a. (0.23 g) in tetrahydrofuran (5 mL) was added triethylamine (0.08 mL). Acetyl chloride (0.04 g) was added, resulting in gas evolution and precipitate formation. After 1 hour, additional triethylamine (0.04 mL) and acetyl chloride (0.02 mL) were added. After 15 minutes, the reaction was diluted with ethyl acetate and washed with water. The aqueous phase was made basic with saturated sodium bicarbonate and extracted with ethyl acetate. The combined organic extracts were washed with brine and dried. Evaporation gave a material which solidified upon further evaporation from dichloromethane:hexane. The solid (0.313 g) was not further purified; TLC: $R_f=0.19$, methanol:dichloromethane (5:95); 300 MHz NMR: 2.15 (s,3), 7.87 (d,1), 8.34 (t,1), 8.82 (s,1), 9.54 (s,1); MS: m/z=508 (M+1).

EXAMPLE 9

2-(5-Acetylamino-6-oxo-2-phenyl-1,6-dihydropyrimidin-1-yl)-NN-[3,3-difluoro-1-isopropyl-2-oxo-3-[N-(4-pyridylmethyl)carbamoyl]propyl]acetamide.

2-(5-Acetylamino-6-oxo-2-phenyl-1,6-dihydropyrimidin-1-yl)-N-[3,3-difluoro-2-hydroxy-1-isopropyl-3-[N-(4-pyridylmethyl)carbamoyl]propyl]acetamide was subjected to conditions similar to those described in Example 1. The crude product was purified by chromatography, with dichloromethane:methanol (gradient, 96:4, 94:6) as the eluent, to afford the title compound; TLC: $R_f=0.24$, methanol:dichloromethane (6:94); MS: m/z=555 (M+1). Analysis for $C_{27}H_{28}F_2N_6O_5.0.55$ $H_2O$: Calculated: C, 57.45; H, 5.20; N, 14.89; Found: C, 57.48; H, 5.16; N, 14.60.

The starting alcohol was prepared as follows.

a. 2-(5-Amino-6-oxo-2-phenyl-1,6-dihydropyrimidin-1-yl)-N-[3,3-difluoro-2-hydroxy-1-isopropyl-3-[N-(4-pyridylmethyl)carbamoyl]propyl]acetamide. 2-(5-Benzyloxycarbonylamino-6-oxo-2-phenyl-1,6-dihydropyrimidin-1-yl)-N-[3,3-difluoro-2-hydroxy-1-isopropyl-3-[N-(4-pyridylmethyl)carbamoyl]propyl]acetamide was subjected to hydrogenolysis conditions similar to those described in Example 8.a., except tetrahydrofuran was used as solvent and the hydrogen pressure was 3.5 bar. The crude product was purified by chromatography, with dichloromethane:methanol (gradient, 96:4, 94:6, 92:8) to give the amine; TLC: $R_f=0.21$, methanol:dichloromethane (8:92); MS: m/z=515 (M+1).

b. 2-(5-Acetylamino-6-oxo-2-phenyl-1,6-dihydropyrimidin-1-yl)-N-[3,3-difluoro-2-hydroxy-1-isopropyl-3-[N-(4-pyridylmethyl)carbamoyl]propyl]acetamide. The product from Example 9.a. was subjected to acylation conditions similar to those described in Example 8.b. The crude product was purified by chromatography, with dichloromethane:methanol (gradient, 97:3, 96:4, 94:6) as the eluent; TLC: $R_f=0.11$, methanol:dichloromethane (4:96); MS: m/z=556 (M+1).

EXAMPLE 10

2-(5-Acetylamino-6-oxo-2-phenyl-1,6-dihydropyrimidin-1-yl)-N-[3,3-difluoro-1-isopropyl-2-oxo-3-[N-[2-(2-pyridyl)ethyl]carbamoyl]propyl]acetamide.

2-(5-Amino-6-oxo-2-phenyl-1,6-dihydropyrimidin-1-yl)-N-[3,3-difluoro-1-isopropyl-2-oxo-3-[N-[2-(2-pyridyl)ethyl]carbamoyl]propyl]acetamide was subjected to a procedure similar to that described in Example 8.b. The crude product was purified by chromatography, with dichloromethane:methanol (95:5) as the eluent, to afford the title compound; TLC: $R_f=0.33$, methanol:dichloromethane (5:95); MS: m/z=569 (M+1). Analysis for $C_{28}H_{30}F_2N_6O_5.0.4$ $H_2O$: Calculated: C, 58.41; H, 5.39; N, 14.60; Found: C, 58.47; H, 5.32; N, 14.21.

EXAMPLE 11

2-[6-Oxo-2-phenyl-5-(4-pyridylmethoxycarbonylamino)-1,6-dihydropyrimidin-1-yl]-N-[3,3-difluoro-1-isopropyl-2-oxo-3-(N-phenethylcarbamoyl)propyl]acetamide.

2-(5-Amino-6-oxo-2-phenyl-1,6-dihydropyrimidin-1-yl)-N-[3,3-difluoro-1-isopropyl-2-oxo-3-(N-phenethylcarbamoyl)propyl]acetamide (0.140 g) in tetrahydrofuran (2 mL) was cooled in a salt/ice-water bath. After triethylamine (0.045 mL) was added, a solution of triphosgene (0.030 g) in tetrahydrofuran (0.5 mL) was added dropwise. Two 0.5 mL rinses of the syringe were also added to the reaction mixture. The mixture was stirred in a salt/ice-water bath for 40 minutes. Solid 4-pyridylcarbinol (0.058 g) was added and the mixture was allowed to slowly warm to room temperature. Tetrahydrofuran (1.5 mL) was added to the solution and it was allowed to stir overnight. The mixture was diluted with ethyl acetate and washed with saturated bicarbonate. The organic phase was washed with brine, dried and evaporated to give an oil. Chromatography, with dichloromethane:methanol (gradient, 98:2 to 95:5 to 90:10) as the eluent, followed by drying under vacuum, gave the title compound as a white solid (0.06 g); TLC: $R_f=0.45$, methanol:dichloromethane (10:90); 300 MHz NMR (DMSO/trifluoroacetic acid): 0.77 (d,3), 0.89 (d,3), 2.20–2.40 (m,1), 2.80 (t,2), 3.33–3.45 (m,2), 4.64 (q,2), 4.87 (d,1), 5.57 (s,2), 7.20–7.32 (m,5), 7.47–7.62 (m,5), 8.23 (d,2), 8.56 (s,1), 9.00 (d,2), 9.25 (t,1); MS: m/z=661 (M+1). Analysis for $C_{34}H_{34}F_2N_6O_6$: Calculated: C, 61.81; H, 5.19; N, 12.72; Found: C, 62.07; H, 5.47; N, 12.67.

EXAMPLE 12

2-[6-Oxo-2-phenyl-5-(4-pyridylmethoxycarbonylamino)-1,6-dihydropyrimidn-1-yl]-N-[3,3-difluoro-1-isopropyl-2-oxo-3-(N-propylcarbamoyl)propyl]acetamide.

2-(5-Amino-6-oxo-2-phenyl-1,6-dihydropyrimidin-1-yl)-N-[3,3-difluoro-1-isopropyl-2-oxo-3-(N-propylcarbamoyl)propyl]acetamide was subjected to a procedure similar to that described in Example 11. The crude product was purified by chromatography, with chloroform:methanol (96:4) as the eluent, to give the title compound; TLC: $R_f$=0.29, ethanol:chloroform (4:96); MS: m/z=599 (M+1). Analysis for $C_{29}H_{32}F_2N_6O_6$: Calculated: C, 58.18; H, 5.39; N, 14.04; Found: C, 58.40; H, 5.46; N, 13.83.

EXAMPLE 13

2-[5-Amino-2-(4-fluorophenyl)-6-oxo-1,6-dihydropyrimidin-1-yl]-N-[3,3-difluoro-1-isopropyl-2-oxo-3-[N-(2-morpholinoethyl)carbamoyl]propyl]acetamide.

Using a procedure similar to that described in Example 8.a., 2-[5-benzyloxycarbonylamino-2-(4-fluorophenyl)-6-oxo-1,6-dihydropyrimidin-1-yl]-N-[3,3-difluoro-1-isopropyl-2-oxo-3-[N-(2-morpholinoethyl)-carbamoyl]propyl]acetamide was converted into the title compound; chromatography solvent: dichloromethane:methanol (gradient, 95:5, 9:1); TLC: $R_f$=0.07, dichloromethane:methanol (95:5); MS: m/z=553(M+1). Analysis for $C_{25}H_{31}F_3N_6O_5$.0.30 $CH_3COOC_2H_5$: Calculated: C, 54.35; H, 5.81; N, 14.52; Found: C, 54.05; H, 5.77; N, 14.56.

The starting urethane was prepared as follows.

a. 2-[5-Benzyloxycarbonylamino-2-(4-fluorophenyl)-6-oxo-1,6-dihydropyrimidin-1-yl]-N-(3,3-difluoro-1-isopropyl-2-hydroxy-3-ethoxycarbonylpropyl)acetamide. 2-[5-Benzyloxycarbonylamino-2-(4-fluorophenyl)-6-oxo-1,6-dihydropyrimidin-1-yl]acetic acid (prepared as described in European Patent Application, Publication No. 528633) was subjected to a procedure similar to that described in Example 1.b to give the amide; TLC: $R_f$=0.51, dichloromethane:methanol; MS: m/z=605(M+1).

b. 2-[5-Benzyloxycarbonylamino-2-(4-fluorophenyl)-6-oxo-1,6-dihydropyrimidin-1-yl]-N-[3,3-difluoro-1-isopropyl-2-hydroxy-3-[N-(2-morpholinoethyl)-carbamoyl]propyl]acetamide. Using a procedure similar to that described in Example 1.c., except diluting with water and partially evaporating before extracting, eliminating the 10% hydrochloric acid and saturated sodium bicarbonate washes, and triturating with ether, the amide was prepared; TLC: $R_f$=0.42, dichloromethane:methanol; MS: m/z=689(M+1).

c. 2-[5-Benzyloxycarbonylamino-2-(4-fluorophenyl)-6-oxo-1,6-dihydropyrimidin-1-yl]-N-[3,3-difluoro-1-isopropyl-2-oxo-3-[N-(2-morpholinoethyl)carbamoyl]propyl]acetamide. Using a procedure similar to that described in Example 1, except omitting the 10% hydrochloric acid wash, the ketone was prepared; chromatography solvent: dichloromethane:methanol (gradient, 96:4, 95:5); TLC: $R_f$=0.41, dichloromethane:methanol (95:5); MS: m/z=687(M+1). Analysis for $C_{33}H_{37}F_3N_6O_7$.0.95 $H_2O$: Calculated: C, 56;32; H, 5.57; N, 11.94; Found: C, 56.28; H, 5.63; N, 11.90.

EXAMPLES 14-19

Using a procedure similar to that described in Example 8.a., the following compounds of formula I, wherein R is hydrogen, $R^0$ is isopropyl, and $R^A$ and $R^6$ have the indicated values, were prepared from the corresponding compounds of formula I, wherein R is benzyloxycarbonyl, with exceptions as noted.

Example 14

$R^A$=2-(tert-butoxycarbonyl)ethyl; $R^6$=4-fluorophenyl: Except using ethanol:tetrahydrofuran (2:1) as the solvent; Chromatography solvent: dichloromethane:methanol (93:7); TLC: $R_f$=0.16, dichloromethane:methanol (95:5); MS: m/z=568(M+1). Analysis for $C_{26}H_{32}F_3N_5O_6$: Calculated: C, 55.02; H, 5.68; N, 12.34; Found: C, 54.99; H, 5.77; N, 12.11.

Example 15

$R^A$=2-(4-pyridyl)ethyl; $R^6$=4-fluorophenyl: Except using ethanol:tetrahydrofuran (3:1) as the solvent; TLC: $R_f$=0.40, dichloromethane:methanol (95:5); MS: m/z=545(M+1). Analysis for $C_{26}H_{27}F_3N_6O_4$.0.20 $CH_2Cl_2$: Calculated: C, 56.04; H, 4.92; N, 14.97; Found: C, 56.33; H, 5.11; N, 14.59.

Example 16

$R^A$=2-(dimethylamino)ethyl; $R^6$=4-fluorophenyl: Except using ethanol:tetrahydrofuran (2:1) as the solvent. After filtration the product was partitioned between water and ethyl acetate. The ethyl acetate was washed (brine), dried and evaporated to give the product; TLC: $R_f$=0.072, chloroform:methanol (9:1); MS: m/z=511(M+1). Analysis for $C_{23}H_{29}F_3N_6O_4$.0.40 $H_2O$: Calculated: C, 53.36; H, 5.80; N, 16.23; Found: C, 53.61; H, 5.87; N, 15.84.

Example 17

$R^A$=methyl; $R^6$=4-fluorophenyl: TLC: $R_f$=0.12, dichloromethane:methanol (95:5); MS: m/z=454(M+1). Analysis for $C_{20}H_{22}F_3N_5O_4$: Calculated: C, 52.98; H, 4.89; N, 15.45; Found: C, 53.17; H, 5.06; N, 15.13.

Example 18

$R^A$=methyl; $R^6$=phenyl: Except the starting material was treated once with 10% (w/w) palladium on carbon in tetrahydrofuran for 4 days. Chromatography, with chloroform:methanol (95:5) as the eluent gave the title compound; TLC: $R_f$=0.13, chloroform:methanol (95:5); MS: m/z=436(M+1). Analysis for $C_{20}H_{23}F_2N_5O_4$.0.9 $H_2O$: Calculated: C, 53.19; H, 5.53; N, 15.51; Found: C, 53.45; H, 5.24; N, 15.14.

Example 19

$R^A$=2-morpholinoethyl; $R^6$=phenyl: except using tetrahydrofuran as the solvent; chromatography, with chloroform:methanol (gradient, 95:5, 93:7, 91:9) as the eluent; TLC: $R_f$=0.41; MS: m/z=535(H+1). Analysis for $C_{25}H_{32}F_2N_6O_5$.0.2 $CHCl_3$: Calculated: C, 54.20; H, 5.81; N, 15.05; Found: C, 54.48; H, 5.97; N, 14.94.

The starting materials for Examples 14-19 were prepared as follows.

EXAMPLES 14.a.-19.a.

Using a procedure similar to that described in Example 1.c., but substituting the requisite amine of formula $R^ANH_2$ for the propyl amine used therein and using the requisite ester, the following compounds of formula II, wherein R is benzyloxycarbonyl, $R^0$ is isopropyl and $R^A$ and $R^6$ have the indicated values, were prepared, with exceptions as noted.

14.a. $R^A$=2-(tert-butoxycarbonyl)ethyl; $R^6$=4-fluorophenyl: Except one equivalent of triethylamine was used to generate the free base of the amine; TLC: $R_f$=0.18, chloroform:methanol (40:1); MS: m/z=704(M+1).

15.a. $R^A$=2-(4-pyridyl)ethyl; $R^6$=4-fluorophenyl: Chromatography solvent: chloroform:methanol (gradient, 40:1, 30:1); TLC: $R_f$=0.32, dichloromethane:methanol; MS: m/z=681(M+1).

16.a. $R^4$=2-(dimethylamino)ethyl; $R^6$=4-fluorophenyl: When reaction was complete, the mixture was evaporated; and the residue was partitioned between ethyl acetate and water. The organic phase was washed (saturated ammonium chloride, saturated sodium bicarbonate, water) and triturated with ether to afforded the product; TLC: $R_f$=0.053, dichloromethane:methanol (95:5); MS: m/z=647(M+1).

17.a. $R^4$=methyl; $R^6$=4-fluorophenyl: Except using a 40% aqueous solution of methylamine; TLC: $R_f$=0.11, chloroform:methanol (40:1); MS: m/z=590(M+1).

18.a. $R^4$=methyl; $R^6$=phenyl: Except using a 40% aqueous solution of methylamine. The reaction was diluted with ethyl acetate, washed (1% hydrochloric acid, saturated sodium bicarbonate, brine), dried, and evaporated; Chromatography: dichloromethane:methanol (gradient, 92:2, 97:3); TLC: $R_f$=0.33, dichloromethane:methanol (95:5); MS: m/z=572(M+1).

19.a. $R^4$=2-morpholinoethyl; $R^6$=phenyl: The reaction was diluted with ethyl acetate, washed (saturated sodium bicarbonate, brine), dried, and evaporated to give an off white foam; chromatography: dichloromethane:methanol (97:3); TLC: $R_f$=0.39, dichloromethane:methanol (95:5); MS: m/z=671(M+1).

EXAMPLES 14.b.–19.b.

Using a procedure similar to that described in Example 1, the following compounds of formula I, wherein R is benzyloxycarbonyl, $R^0$ is isopropyl, and $R^4$ and $R^6$ have the indicated values, were prepared from the corresponding alcohols of formula II, described in Examples 14.a.–19.a., with exceptions as noted. It is noted that these products are also Compounds of the invention.

14.b. $R^4$=2-(tert-butoxycarbonyl)ethyl; $R^6$=4-fluorophenyl: Chromatography: chloroform:methanol (40:1); TLC: $R_f$=0.21, chloroform:methanol (40:1); MS: m/z=702(M+1).

15.b. $R^4$=2-(4-pyridyl)ethyl; $R^6$=4-fluorophenyl: Except omitting the 10% hydrochloric acid wash; chromatography solvent: dichloromethane:methanol (gradient, 97:3, 95:5); TLC: $R_f$=0.34, dichloromethane:methanol (95:5); MS: m/z=679(M+1). Analysis for $C_{34}H_{33}F_3N_6O_6$.0.5 $H_2O$: Calculated: C, 59.38; H, 4.98; N, 12.22; Found: C, 59.39; H, 4.99, N, 11.91.

16.b. $R^4$=2-(dimethylamino)ethyl; $R^6$=4-fluorophenyl. Except a saturated ammonium chloride wash was performed; chromatography solvent: dichloromethane:methanol (gradient 95:5, 9:1); TLC: $R_f$=0.18, dichloromethane:methanol (95:5); MS: m/z=645(M+1).

17.b. $R^4$=methyl; $R^6$=4-fluorophenyl: Except a saturated ammonium chloride wash was performed; chromatography solvent: chloroform:methanol (40:1); TLC: $R_f$=0.31, dichloromethane:methanol (95:5); MS: m/z=587(M+1).

18.b. $R^4$=methyl; $R^6$=phenyl: Chromatography, with dichloromethane:methanol (98:2) as eluent, and crystallization from ethyl acetate, ether, and hexane yielded a white powder; TLC: $R_f$=0.48, chloroform:methanol (96:4); MS: m/z=570(M+1). Analysis for $C_{28}H_{29}F_2N_5O_6$: Calculated: C, 59.04; H, 5.13; N, 12.30; Found: C, 58.87; H, 5.15; N, 12.02.

19.b. $R^4$=2-morpholinoethyl; $R^6$=phenyl: Except the recovered crude product was a mixture of starting alcohol and desired ketone. The crude product was retreated as described in Example 1. Chromatography with chloroform:methanol (98:2) as the eluent, gave a white solid; TLC: $R_f$=0.41, dichloromethane:methanol (95:5); MS: m/z=669(M+1). Analysis for $C_{33}H_{38}F_2N_6O_7$.0.1 $H_2O$: Calculated: C, 59.01; H, 6.01; N, 12.53; Found: C, 58.69; H, 5.71; N, 12.39.

EXAMPLES 20–22

Using a procedure similar to that described in Example 5, the following compounds of formula I, wherein R is hydrogen, $R^0$ is isopropyl, and $R^4$ and $R^6$ have the indicated values, were prepared from the corresponding compounds of formula I, wherein R is benzyloxycarbonyl, with exceptions as noted.

Example 20

$R^4$=phenethyl; $R^6$=4-fluorophenyl: Except after quenching, the organic phase was washed with only water. The product was triturated with ether, then crystallized from ethyl acetate/ether. Recrystallization from the same solvents yielded the product; TLC: $R_f$=0.39, dichloromethane:methanol (95:5); MS: m/z=544(M+1). Analysis for $C_{27}H_{28}F_3N_5O_4$: Calculated: C, 59.66; H, 5.19; N, 12.88; Found: C, 60.03; H, 5.26; N, 12.59.

Example 21

$R^4$=2-pyridylmethyl; $R^6$=2-thienyl: Chromatography solvent: tetrahydrofuran:dichloromethane (40:60); TLC: $R_f$=0.2, tetrahydrofuran:dichloromethane (25:75); MS: m/z=519(M+1). Analysis for $C_{25}H_{26}F_2N_6O_6S$: Calculated: C, 53.28; H, 4.66; N, 16.21; Found: C, 53.06; H, 4.72; N, 15.92.

Example 22

$R^4$=pyrrolidino; $R^6$=2-thienyl: Chromatography solvent: methanol:dichloromethane (6:94); TLC: Rf=0.5, methanol:dichloromethane (10:90); MS: m/z=482(M+1). Analysis for $C_{21}H_{25}F_2N_5O_4S$: Calculated: C, 52.38; H, 5.23; N, 14.54; Found: C, 52.59; H, 5.40; N, 13.95.

The starting material urethanes were prepared as follows.

EXAMPLES 20.a.–22.a.

Using a procedure similar to that described in Example 1.c. but substituting the requisite amine of formula $R^4NH_2$ for the propyl amine used therein and using the requisite ester, the following compounds of formula II, wherein R is benzyloxycarbonyl, $R^0$ is isopropyl and $R^4$ and $R^6$ have the indicated values, were prepared, with exceptions as noted.

20.a. $R^4$=phenethyl; $R^6$=4-fluorophenyl: Except in the work-up the reaction was diluted with water, and the pH was adjusted to 6–7 with 10% hydrochloric acid and saturated sodium bicarbonate. The mixture was then evaporated. The residue was disolved in ethyl acetate, washed (water, saturated ammonium chloride, 10% hydrochloric acid, brine), and dried. The foam was triturated with ether to give the amide; TLC: $R_f$=0.17, chloroform:methanol (40:1); MS: m/z=680(M+1).

21.a. $R^4$=2-pyridylmethyl; $R^6$=2-thienyl: Chromatography solvent: tetrahydrofuran:dichloromethane (10:90); TLC: $R_f$=0.25, tetrahydrofuran:dichloromethane (5:95); MS: m/z=655(M+1).

22.a. $R^4$=pyrrolidino; $R^6$=2-thienyl: Chromatography solvent: methanol:dichloromethane (5:95); TLC:

$R_f$=0.4, tetrahydrofuran:dichloromethane (10:90); MS: m/z=618(M+1).

EXAMPLES 20.b.–22.b.

Using a procedure similar to that described in Example 1 the following compounds of formula I, wherein R is benzyloxycarbonyl, $R^0$ is isopropyl, and $R^4$ and $R^6$ have the indicated values, were prepared from the corresponding alcohols of formula II, described in Examples 20.a.–23.a., with exceptions as noted. It is noted that these products are also Compounds of the invention.

20.b. $R^4$=phenethyl; $R^6$=4-fluorophenyl: Except the mixture was diluted with saturated aqueous sodium bicarbonate and washed with 10% hydrochloric acid. The resulting material was chromatographed twice, with chloroform:methanol (gradient 50:1, 40:1) as the eluent, to give the desired compound; TLC: $R_f$=0.42, dichloromethane:methanol (95:5); MS: m/z=678(M+1).

21.b. $R^4$=2-pyridylmethyl; $R^6$=2-thienyl: Chromatography solvent: tetrahydrofuran:dichloromethane (10:90); TLC: $R_f$=0.7, tetrahydrofuran:dichloromethane (25:75); MS: m/z=653(M+1).

22.b. $R^4$=pyrrolidino; $R^6$=2-thienyl: Chromatography solvent: tetrahydrofuran:dichloromethane (6:94); TLC: $R_f$=0.6, tetrahydrofuran:dichloromethane (10:90); MS: m/z=616(M+1).

EXAMPLE 23

2-[5-Benzyloxycarbonylamino-6-oxo-2-(2-thienyl)-1,6-dihydropyrimidin-1-yl]-N-[3,3-difluoro-1-isopropyl-2-oxo-3-[N-(carboxymethyl)carbamoyl]propyl]acetamide.

The compound described in part c. below was subjected to a procedure similar to that described in Example 24, except that the reaction was run in neat trifluoroacetic acid; crystallized from ether to afford the title compound; TLC: $R_f$=0.7, tetrahydrofuran:dichloromethane (8:92); MS: m/z=620(M+1). Analysis for $C_{27}H_{27}F_2N_5O_8S$: Calculated: C, 52.34; H, 4.39; N, 11.30; Found: C, 51.68; H, 4.55; N, 10.75.

The starting material ester was prepared as follows.

a. 2-[5-Benzyloxycarbonylamino-6-oxo-2-(2-thienyl)-1,6-dihydropyrimidin-1-yl]-N-[3,3-difluoro-1-isopropyl-2-hydroxy-3-[N-(tert-butoxycarbonylmethyl)carbamoyl]propyl]acetamide. The compound described at Example 27.a. and tert-butyl glycine were subjected to a procedure similar to that described in Example 1.c. to give the alcohol, which was crystallized from ether:hexane (1:1) to afford the product; TLC: $R_f$=0.5, tetrahydrofuran:dichloromethane (5:95); MS: m/z=678(M+1).

b. 2-[5-Benzyloxycarbonylamino-6-oxo-2-(2-thienyl)-1,6-dihydropyrimidin-1-yl]-N-[3,3-difluoro-1-isopropyl-2-oxo-3-[N-(tert-butoxycarbonylmethyl)carbamoyl]propyl]acetamide. The compound described at part a. was subjected to a procedure similar to that described in Example 1 to give the ketone; chromatography: tetrahydrofuran:dichloromethane (6:94); TLC: $R_f$=0.6, tetrahydrofuran:dichloromethane (10:90); MS: m/z=676(M+1). This product is also a Compound of the invention.

EXAMPLE 24

2-[5-Benzyloxycarbonylamino-2-(4-fluorophenyl)-6-oxo-1,6-dihydropyrimidin-1-yl]-N-[3,3-difluoro-1-isopropyl-2-oxo-3-[N-(2-carboxyethyl)carbamoyl]propyl]acetamide.

To a solution of the compound described at Example 14.b. (0.208 g) in dichloromethane (2 mL) was added trifluoroacetic acid (0.34 mL). When the reaction was complete the mixture was partitioned between water and ethyl acetate. The organic phase was washed (brine) and dried. The solvent was evaporated to provide the title compound as a white solid; TLC: $R_f$=0.10, dichloromethane:methanol:acetic acid (97:2:1); MS: m/z=646(M+1). Analysis for $C_{30}H_{30}F_3N_5O_8$: Calculated: C, 55.81; H, 4.68; N, 10.85; Found: C, 55.69; H, 4.86; N, 10.51.

EXAMPLE 25

2-[5-Amino-2-(4-fluorophenyl)-6-oxo-1,6-dihydropyrimidin-1-yl]-N-[3,3-difluoro-1-isopropyl-2-oxo-3-[N-[2-(4-pyridyl)ethyl]carbamoyl]propyl]acetamide.

Using a procedure similar to that described in Example 8.a. the compound described at Example 24 was converted into the title compound, with the following exceptions to the procedure. The solvent used was ethanol:tetrahydrofuran (2:1). After concentration, the resulting oil was partioned in ethyl acetate and water. The organic phase was washed with brine. The combined aqueous phases were extracted with ethyl acetate. The combined organics were dried and evaporated. Precipitation from hot ethyl acetate by the addition of hexane afforded the title compound; MS: m/z=512(M+1). Analysis for $C_{22}H_{24}F_3N_5O_6$: Calculated: C, 51.66; H, 4.73; N, 13.69; Found: C, 50.77; H, 4.81; N, 13.00.

EXAMPLE 26

2-[5-Amino-6-oxo-2-(4-fluorophenyl)-1,6-dihydropyrimidin-1-yl]-N-[3,3-difluoro-1-isopropyl-2-oxo-3-[N-(tert-butoxycarbonylmethyl)carbamoyl]propyl]acetamide.

Using a procedure similar to that described in Example 8.a., except with ethanol:tetrahydrofuran (2:1) as the solvent, the title compound was prepared. Chromatography solvent: dichloromethane:methanol (96:4); TLC: $R_f$=0.25, dichloromethane:methanol (95:5); MS: m/z=554(M+1). Analysis for $C_{25}H_{30}F_3N_5O_6 \cdot 0.3 H_2O$: Calculated: C, 53.72; H, 5.52; N, 12.53; Found: C, 53.68; H, 5.48; N, 12.45.

The starting material was prepared as follows.

a. 2-[5-Benzyloxycarbonylamino-2-(4-fluorophenyl)-6-oxo-1,6-dihydropyrimidin-1-yl]-N-[3,3-difluoro-1-isopropyl-2-hydroxy-3-[N-(tert-butoxycarbonylmethyl)carbamoyl]propyl]acetamide.

Glycine tert-butyl ester hydrochloride was subjected to a procedure similar to that described in Example 14.a. When reaction was complete, the mixture was evaporated and stirred in water. The resulting solid was collected, and trituration from ether yielded the product; TLC: $R_f$=0.22, dichloromethane:methanol; MS: m/z=690(M+1).

b. 2-[5-Benzyloxycarbonylamino-2-(4-fluorophenyl)-6-oxo-1,6-dihydropyrimidin-1-yl]-N-[3,3-difluoro-1-isopropyl-2-oxo-3-[N-(tert-butoxycarbonylmethyl)carbamoyl]propyl]acetamide. The procedure was similar to Example 1 except that a 10% hydrochloric acid wash was done. Chromatography solvent: chloroform:methanol (40:1); TLC: $R_f$=0.5, chloroform:methanol (40:1); MS: m/z=688(M+1). This product is also a Compound of the invention.

EXAMPLE 27

2-[5-Amino-6-oxo-2-(2-thienyl)-1,6-dihydropyrimidin-1-yl]-N-[3,3-difluoro-1-isopropyl-2-oxo-3-(N-methylcarbamoyl)propyl]acetamide.

Using a procedure similar to that described in Example 5, the corresponding urethane was converted into the title compound; chromatography solvent: tetrahydrofuran:dichloromethane (40:60); TLC: $R_f$=0.3, tetrahydrofuran:dichloromethane (35:65); NMR: 0.80 (d,3), 0.89 (d,3), 2.27 (m,1), 2.67 (d,3), 4.84 (m,3), 5.31 (d,1), 7.06 (t,1), 7.16 (d,1), 7.29 (s,1), 7.68 (d,1), 8.74 (d,1), 9.08 (d,1); MS: m/z=442 (M+1). Analysis for $C_{18}H_{21}F_2N_5O_4S$: Calculated: C, 48.97; H, 4.79; N, 15,86; Found: C, 49.02; H, 4.96; N, 15,61.

The starting alcohol was prepared as follows.
a. 2-[5-Benzyloxycarbonylamino-6.oxo-2-(2-thienyl)-1,6-dihydropyrimidin-1-yl]-N-(3,3-difluoro-1-isopropyl-2-hydroxy-3-ethoxycarbonylpropyl)acetamide. 2-[5-Benzyloxycarbonyamino-6-oxo-2-(2-thienyl)-1,6-dihydropyrimidin-1-yl]acetic acid (prepared as described in Euorpean Patent Application, Publication No. 528633) and the hydrobromide salt from Example 1.a. were subjected to a procedure similar to that described in Example 1.b. to give the alcohol; chromatography solvent: tetrahydrofuran:dichloromethane (10:90); TLC: $R_f$=0.4, tetrahydrofuran:dichloromethane (10:90); MS: m/z=593(M+1).
b. 2-[5-Benzyloxycarbonylamino-6-oxo-2-(2-thienyl)-1,6-dihydropyrimidin-1-yl]-N-[3,3-difluoro-1-isopropyl-2-hydroxy-3-(N-methylcarbamoyl)propyl]acetamide. Using a procedure similar to that described in Example 1.c., except substituting methylamine (40% aqueous solution) for the propylamine used therein, the amide was prepared; crystallized from ether:hexane (1:1); TLC: $R_f$=0.3, tetrahydrofuran:dichloromethane (10:90); MS: m/z=578(M+1).
c. 2-[5-Benzyloxycarbonylamino-6-oxo-2-(2-thienyl)-1,6-dihydropyrimidin-1-yl]-N-[3,3-difluoro-1-isopropyl-2-oxo-3-(N-methylcarbamoyl)propyl]acetamide. 2-[5-Benzyloxycarbonylamino-6-oxo-2-(2-thienyl)-1,6-dihydropyrimidin-1-yl]-N-[3,3-difluoro-1-isopropyl-2-hydroxy-3-(N-methylcarbamoyl)propyl]acetamide was subjected to a procedure similar to that described in Example 1 to give the ketone; chromatography solvent: tetrahydrofuran:dichloromethane (15:85); TLC: $R_f$=0.5, tetrahydrofuran:dichloromethane (15:85); MS: m/z=576(M+1). This product is also a Compound of the invention.

EXAMPLE 28

2-(5-Amino-6-oxo-2-phenyl-1,6-dihydropyrimidin-1-yl)-N-[3,3-difluoro-1-isopropyl-2-oxo-3-[N-(2-tert-butoxycarbonyl)-carbamoyl]propyl]acetamide.

2-(5-Benzyloxycarbonylamino-6-oxo-2-phenyl-1,6-dihydropyrimidin-1-yl)-N-[3,3-difluoro-1-isopropyl-2-oxo-3-[N-[2-(tert-butoxycarbonyl)ethyl]carbamoyl]propyl]acetamide was subjected to conditions similar to those described in Example 8.a., except a mixture of ethanol and tetrahydrofuran was used and after 24 hours additional catalyst was added without removing the spent catalyst. Chromatography, with chloroform:ethyl acetate (85:15) and chloroform:methanol (98:2) as the eluent, afforded the title compound; TLC: $R_f$=0.24, chloroform: methanol (96:4); MS: m/z=550(M+1). Analysis for $C_{26}H_{33}F_2N_5O_6$.0.6 $H_2O$: Calculated: C, 55.72; H, 6.15; N, 12.50; Found: C, 55.86; H, 6.14; N, 12.47.

The starting urethane was prepared as follows.
a. 2-(5-Benzyloxycarbonylamino-6-oxo-2-phenyl-1,6-dihydropyrimidin-1-yl)-N-[3,3-difluoro-1-isopropyl-2-hydroxy-3-[N-[2-(tertbutoxycarbonyl)ethyl]-carbamoyl]propyl]acetamide. To a solution of the product described at Example 1.b. (1.66 g) in ethanol (30 mL) was added triethylamine (1.4 mL) and β-alanine tert-butyl ester hydrochloride (1.70 g). After 24 hours additional triethylamine (0.95 mL) and β-alanine tert-butyl ester hydrochloride (1.13 g) were added. After 2.5 days the reaction mixture was evaporated, the solids triturated with water, collected by filtration, washed (water, ether, hexane) and dried under vacuum to yield the title compound as a white solid; TLC: $R_f$=0.30, chloroform:ethyl acetate (6:4); MS: m/z=686(M+1).
b. 2-(5-Benzyloxycarbonylamino-6-oxo-2-phenyl-1,6-dihydropyrimidin-1-yl)-N-[3,3-difluoro-1-isopropyl-2-oxo-3-[N-[2-(tert-butoxycarbonyl)ethyl]carbamoyl]propyl]acetamide. The compound described at part a. was subjected to conditions similar to those described in Example 1, except the reaction was washed (10% hydrochloric acid, saturated sodium bicarbonate, brine) to give the ketone; chromatography, with dichloromethane:methanol (gradient, 99:1, 98:2) as eluent, afforded the product; TLC: $R_f$=0.35, chloroform:methanol (96:4); MS: m/z=684(M+1). This product is also a Compound of the invention.

EXAMPLE 29

2-(5-Amino-6-oxo-2-phenyl-1,6-dihydropyrimidin-1-yl)-N-[3,3-difluoro-1-isopropyl-2-oxo-3-[N-(tert-butoxycarbonylmethyl)carbamoyl]propyl]acetamide.

To a solution of 2-(5-benzyloxycarbonylamino-6-oxo-2-phenyl-1,6-dihydro-pyrimidin-1-yl)-N-[3,3-difluoro-1-isopropyl-2-oxo-3-[N-(tert-butoxycarbonylmethyl)carbamoyl]propyl]acetamide (0.20 g) in ethanol (1 mL) and tetrahydrofuran (2 mL) was added 10% (v/v) palladium on carbon (0.075 g), and the mixture was shaken under a hydrogen atmosphere (3 bar) for 2.5 hours. The mixture was filtered through diatomaceous earth and evaporated. Chromatography, with chloroform:methanol (96:4) as the eluent, gave material which was precipitated from dichloromethane and hexane to yield the title compound as a white solid (0.128 g); TLC: $R_f$=0.35, chloroform:methanol (96:4); MS: m/z=498(M+1). Analysis for $C_{24}H_{31}F_2N_5O_6$.0.3 $H_2O$: Calculated: C, 55.51; H, 5.89; N, 12.95; Found: C, 55.65; H, 5.73; N, 12.60.

The starting urethane was prepared as follows.
a. 2-(5-Benzyloxycarbonylamino-6-oxo-2-phenyl-1,6-dihydropyrimidin-1-yl)-N-[3,3-difluoro-1-isopropyl-2-hydroxy-3-[N-(tert-butoxycarbonylmethyl)-carbamoyl]propyl]acetamide. To a solution of the product described at Example 1.b. (1.05 g) in tetrahydrofuran (17 mL) was added triethylamine (0.82 mL) and glycine tert-butylester hydrochloride (0.990 g). After 18 hours, additional triethylamine (0.30 mL) and glycine tert-butylester hydrochloride (0.33 g) were added. The additions were repeated after 1 day, and the reaction mixture stirred for 1 day. The mixture was evaporated and the solids were triturated with water, collected by filtration, washed (water, ether, hexane), and dried under vacuum to yield the title compound as a white powder; TLC: $R_f=0.47$, chloroform:methanol (97:3); m/z=672(M+1).

b. 2-(5-Benzyloxycarbonylamino-6-oxo-2-phenyl-1,6-dihydropyrimidin-1-yl)-N-[3,3-difluoro-1-isopropyl-2-oxo-3-[N-(tert-butoxycarbonylmethyl)carbamoyl]propyl]acetamide. The compound described at part a. was subjected to conditions similar to those described in Example 1 to give the ketone; chromatography, chloroform:ethyl acetate (85:15); TLC: $R_f=0.38$, chloroform:ethyl acetate (85:15); MS: m/z=670(M+1). This product is also a Compound of the invention.

EXAMPLE 30

2-(5-Amino-6-oxo-2-phenyl-1,6-dihydropyrimidin-1-yl]-N-[3,3-difluoro-1-isopropyl-2-oxo-3-[N-[2-(4-pyridyl)ethyl]carbamoyl]propyl]acetamide.

Using a procedure similar to that described in Example 5, 2-(5-benzyloxycarbonylamino-6-oxo-2-phenyl-1,6-dihydropyrimidin-1-yl)-N-[3,3-difluoro-1-isopropyl-2-oxo-3-[N-[2-(4-pyridyl)ethyl)carbamoyl]propyl]acetamide, purifying by chromatography, with chloroform:methanol (94:6), as the eluent, was converted into the title compound; TLC: $R_f=0.21$, dichloromethane:methanol (93:7); MS: m/z=527(M+1). Analysis for $C_{26}H_{28}F_2N_6O_4 \cdot 0.3$ $CHCl_3 \cdot 0.5$ $H_2O$: Calculated: C, 55.29; H, 5.17; N, 14.71; Found: C, 55.09; H, 5.07; N, 14.51.

The starting urethane was prepared as follows.

a. 2-(5-Benzyloxycarbonylamino-6-oxo-2-phenyl-1,6-dihydropyrimidin-1-yl)-N-[3,3-difluoro-1-isopropyl-2-hydroxy-3-[N-[2-(4-pyridyl)ethyl]carbamoyl]propyl]acetamide. Reaction was performed as described in Example 1.c. except that 2-(4-pyridyl)ethylamine was used in place of propylamine and the reaction was evaporated. The residue was dissolved in ethyl acetate, washed (water, brine), dried, and evaporated. Chromatography, with chloroform:methanol (gradient, 97:3, 95:5) as eluent, yielded the alcohol; TLC: $R_f=0.25$, chloroform:methanol (95:5).

b. 2-(5-Benzyloxycarbonylamino-6-oxo-2-phenyl-1,6-dihydropyrimidin-1-yl)-N-[3,3-difluoro-1-isopropyl-2-oxo-3-[N-[2-(4-pyridyl)ethyl)carbamoyl]-propyl]acetamide. The compound described in part a. was subjected to conditions similar to those described in Example 1. Multiple use of chromatography (first column) with chloroform:methanol (gradient, 97:3, 94:6), (second column) chloroform:methanol (98:2), (chromatotron-2 mm plate: flow 6 mL/min) dichloromethane:methanol (gradient, 98:2, 96:4) yielded the title compound; TLC: $R_f=0.21$, dichloromethane:methanol (97:3); MS: m/z=661(M+1). Analysis for $C_{34}H_{34}F_2N_6O_6 \cdot 0.7$ $H_2O$: Calculated: C, 60.65; H, 5.30; N, 12.48; Found: C, 60.62; H, 5.24; N, 12.39. This product is also a Compound of the invention.

EXAMPLES 31–41

Using a procedure similar to that described in Example 8.b., but substituting the requisite chloroformate or anhydride for the acetyl chloride used therein, the following compounds of formula I, wherein $R^0$ is isopropyl and R, $R^4$ and $R^6$ have the indicated values, were prepared from the corresponding amines of formula I, wherein R is hydrogen, with exceptions as noted.

Example 31

R=methoxycarbonyl; $R^4$=methyl; $R^6$=4-fluorophenyl: When reaction was complete, the mixture was evaporated, water was added, and the resulting solid was collected. The aqueous phase was extracted with ethyl acetate. The ethyl acetate was washed (brine), dried, and evaporated to yield a glass which solidified with ether-hexane addition. That solid was combined with the first crop, and both were triturated with ether; TLC: $R_f=0.17$, chloroform:methanol (40:1); MS: m/z=512(M+1). Analysis for $C_{22}H_{24}F_3N_5O_6 \cdot 0.5$ $H_2O$: Calculated: C, 50.77; H, 4.84; N, 13.46; Found: C, 50.95; H, 4.67; N, 13.45.

Example 32

R=trifluoroacetyl; $R^4$=ethyl; $R^6$=4-fluorophenyl: When reaction was complete, the reaction was partitioned between ethyl acetate and water. The ethyl acetate was washed (saturated sodium bicarbonate, saturated ammonium chloride, brine), evaporated, and the residue purified by chromatography, with dichloromethane:methanol (95:5) as the eluent, to afford the product; TLC: $R_f=0.38$, dichloromethane:methanol (95:5); MS: m/z=550(M+1). Analysis for $C_{22}H_{21}F_6N_5O_5$: Calculated: C, 48.09; H, 3.85; N, 12.75; Found: C, 48.40; H, 4.22; N, 12.35.

Example 33

R=trifluoroacetyl; $R^4$=2-(morpholino)ethyl; $R^6$=4-fluorophenyl: Chromatography solvent: dichloromethane:methanol (95:5); TLC: $R_f=0.24$, dichloromethane:methanol; MS: m/z=649(M+1). Analysis for $C_{27}H_{30}F_6N_6O_6$: Calculated: C, 50.00; H, 4.66; N, 12.96; Found: C, 50.00; H, 4,80; N, 12.54.

Example 34

R=methoxycarbonyl; $R^4$=phenethyl; $R^6$=4-fluorophenyl: Chromatography solvent: dichloromethane:methanol (97:3); TLC: $R_f=0.50$, dichloromethane:methanol; MS: m/z=602(M+1). Analysis for $C_{29}H_{30}F_3N_5O_6 \cdot 0.35$ $H_2O$: Calculated: C, 57.30; H, 5.09; N, 11.52; Found: C, 57.29; H, 5.02; N, 11.39.

Example 35

R=trifluoroacetyl; $R^4$=phenethyl; $R^6$=4-fluorophenyl: Except that sodium carbonate was substituted for triethylamine. Chromatography solvent: dichloromethane:methanol (95:5); TLC: $R_f=0.27$, dichloromethane:methanol (95:5); MS: m/z=640(M+1). Analysis for $C_{29}H_{27}F_6N_5O_5$: Calculated: C, 54.46; H, 4.46; N, 10.95; Found: C, 54.73; H, 4.43; N, 10.89.

Example 36

R=trifluoroacetyl; $R^4$=2-(4-pyridyl)ethyl; $R^6$=4-fluorophenyl: Except the aqueous phase was extracted with ethyl acetate, as well as dichloromethane. Chromatography solvent: dichloromethane:methanol (95:5); TLC: $R_f=0.65$, dichloromethane:methanol (9:1); MS: m/z=641(M+1). Analysis for $C_{28}H_{26}F_6N_6O_5$: Calculated: C, 52.50; H, 4.09; N, 13.20; Found: C, 52.19; H, 4.38; N, 12.40.

Example 37

R=methoxycarbonyl; $R^4$=methyl; $R^6$=2-thienyl: Except that sodium carbonate was substituted for triethylamine. Chromatography solvent: tetrahydrofuran:dichloromethane (20:80); TLC: $R_f=0.5$, tetrahydrofuran:dichloromethane (20:80); MS: m/z=500(M+1). Analysis for $C_{20}H_{23}F_2N_5O_6S$: Calculated: C, 48.09; H, 4.64; N, 14.02; Found: C, 47.80; H, 4.43; N, 13.92.

Example 38

R=isopropoxycarbonyl; $R^4$=methyl; $R^6$=2-thienyl: Except that sodium carbonate was substituted for triethylamine. Chromatography solvent: tetrahydrofuran:dichloromethane (10:80); TLC: $R_f$=0.7, tetrahydrofuran:dichloromethane (20:80); MS: m/z=528(M+1). Analysis for $C_{22}H_{27}F_2N_5O_6S$: Calculated: C, 50.09; H, 5.16; N, 13.28; Found: C, 49.94; H, 5.17; N, 13.14.

Example 39

R=methoxycarbonyl; $R^4$=2-pyridylmethyl; $R^6$=2-thienyl: Except sodium carbonate was substituted for triethylamine. Crystallized from ether; TLC: $R_f$=0.4, tetrahydrofuran:dichloromethane (20:80); MS: m/z=577(M+1). Analysis for $C_{25}H_{26}F_2N_6O_6S$: Calculated: C, 52.08; H, 4.54; N, 14.58; Found: C, 51.49; H, 4.62; N, 14.11.

Example 40

R=methoxycarbonyl; $R^4$=cyclopentyl; $R^6$=2-thienyl: Except that sodium carbonate was substituted for triethylamine; Chromatography: methanol:dichloromethane (4:96); TLC: $R_f$=0.7, tetrahydrofuran:dichloromethane (20:80); MS: m/z=540(M+1). Analysis for C23H27F2N5O6S: Calculated: C, 51.20; H, 5.04; N, 12.98; Found: C, 51.23; H, 5.13; N, 12.81.

Example 41

R=methoxycarbonyl; $R^4$=4-chlorophenylsulfonylaminocarbonylmethyl; $R^6$=2-thienyl: Except that sodium carbonate was substituted for triethylamine; Chromatography: methanol:dichloromethane:acetic acid (5:94:1); TLC: $R_f$=0.3, methanol:dichloromethane:acetic acid (5:94:1); MS: m/z=717 (M+1). Analysis for C27H27F2N6O9S2: Calculated: C, 45.22; H, 3.79; N, 11.72; Found: C, 45.51; H, 3.97; N, 11.51.

EXAMPLES 42–57

The following compounds of formula I, wherein $R^0$ is isopropyl and R, $R^4$ and $R^6$ have the indicated values, were prepared using the procedures described.

Example 42

R=hydrogen; $R^4$=4-chlorophenylsulfonylaminocarbonylmethyl; $R^6$=2-thienyl: The compound described at Example 46 was subjected to a procedure similar to that described in Example 5 to yield the title compound; Chromatography solvent: (gradient elution, methanol:dichloromethane:acetic acid (4:95:1) to (10:89:1); TLC: $R_f$=0.25, methanol:dichloromethane:acetic acid (5:94:1); MS: m/z=659(M+1). Analysis for $C_{25}H_{25}ClF_2N_6O_7S_2$: Calculated: C, 45.56; H, 3.82; N, 12.75; Found: C, 45.74; H, 3.99; N, 12.31.

Example 43

R=benzyloxycarbonylamino; $R^4$=carboxymethyl; $R^6$=4-fluorophenyl: The preparation was performed analogously to the procedure described for Example 24. When reaction was complete, the reaction mixture was evaporated and partitioned between ethyl acetate and water. The ethyl acetate phase was washed (brine) and dried. The product was partitioned between ethyl acetate and 10% hydrochloric acid. Redrying and evaporation afforded the product; TLC: $R_f$=0.061, dichloromethane:methanol:acetic acid (97:2:1); MS: m/z=632(M+1), 630(M−1). Analysis for $C_{29}H_{28}F_3N_5O_8$.0.95 $H_2O$: Calculated: C, 53.70; H, 4.65; N, 10.80; Found: C, 53,71; H, 4.42; N, 10.71.

Example 44

R=benzyloxycarbonylamino; $R^4$=carboxymethyl; $R^6$=phenyl: The corresponding tert-butyl ester (0.545 g) was treated with trifluoroacetic acid (5 mL) for 0.5 hour. The reaction mixture was partitioned between water and ethyl acetate. The ethyl acetate portion was washed (water, brine), dried, and evaporated to give a white foam. Trituration with ether and hexane gave the title compound as a white solid (0.134 g); TLC: $R_f$=0.33, chloroform:methanol:acetic acid (89:10:1); MS: m/z=614(M+1). Analysis for $C_{29}H_{29}F_2N_5O_8$.0.3 $H_2O$: Calculated: C, 56.27; H, 4.82; N, 11.31; Found: C, 56.46; H, 4.93; N, 10.94.

Example 45

R=benzyloxycarbonylamino; $R^4$=2-(Phenylsulfonylaminocarbonyl)ethyl; $R^6$=4-fluorophenyl: To the product of Example 24 (0.300 g) in tetrahydrofuan (4 mL) were added 1-(3-dimethylaminopropyl)-3-ethylcarbodiimide hydrochloride (0.094 g), 1-hydroxybenzotriazole hydrate (0.066 g), 4-dimethylaminopyridine (0.060 g), and benzenesulfonamide (0.077 g). After overnight stirring, additional quantities of reagents were added: 1-(3-dimethylaminopropyl)-3-ethylcarbodiimide hydrochloride (0.045 g), 1-hydroxybenzotriazole hydrate (0.031 g), and benzenesulfonamide (0.037 g), plus 4-methylmorpholine (0.054 mL) and tetrahydrofuran (1 mL). The reaction mixture was partitioned between ethyl acetate and 10% hydrochloric acid several times. The ethyl acetate phase was washed (brine), dried and evaporated. The resulting material was purified by chromatography, with dichloromethane:methanol (97:3, 9:1) as the eluent. That product was further purified by reversed phase chromatography, with methanol:water (65:35) as the eluent. The appropriate fractions were partially evaporated, and the aqueous residue was acidified to pH 1 with 10% hydrochloric acid. The resulting precipitate was collected, dissolved in dichloromethane, filtered, evaporated and dried to give the product as a solid; RP-TLC: $R_f$=0.25, methanol:water (65:35) buffered with 0.1% $NaHCO_3$ (pH=6); MS: m/z=785(M+1). Analysis for $C_{36}H_{35}F_3N_6O_9S$: Calculated: C, 55.10; H, 4.50; N, 10.71; Found: C, 54.75; H, 4.25; N, 10.55.

Example 46

R=benzyloxycarbonylamino; $R^4$=4-chlorophenylsulfonylaminocarbonylmethyl; $R^6$=2-thienyl: A solution of the compound described at Example 23 (0.39 g) and 4-chlorobenzenesulfonamide (0.3 g) was dissolved in tetrahydrofuran, and to this was added 1-(3-dimethylaminopropyl)-3-ethylcarbodiimide hydrochloride (0.21 g), and 4-dimethylaminopyridine (0.13 g). The resulting solution was allowed to stir for 12 hours. The reaction mixture was diluted with ethyl acetate and washed (1N hydrochloric acid, water) dried and evaporated to give an oil which was purified by chromatography (gradient elution, tetrahydrofuran:dichloromethane (30:70) to methanol:dichloromethane:acetic acid (5:94:1)) to provide the title compound (0.45 g): TLC: $R_f$=0.3, methanol:dichloromethane:acetic acid (5:94:1);

MS: m/z=793(M+1). Analysis for C$_{33}$H$_{31}$ClF$_2$N$_6$O$_9$S$_2$: Calculated: C, 49.97; H, 3.94; N, 10.59; Found: C, 50.18; H, 4.07; N, 10.67.

Example 47

R=methyl; R$^4$=phenethyl; R$^6$=4-fluorophenyl: To a solution of the compound described in part a. below (0.26 g) in tetrahydrofuran (5 mL) was added water (1 mL) and potassium carbonate (0.275 g). When reaction was complete, the mixture was partitioned between dichloromethane and water. The resulting emulsion was dispersed by addition of water and sodium chloride. The aqueous phase was extracted with ethyl acetate. Each organic phase was washed separately with brine, combined, dried and evaporated. The residue was purified by chromatography, eluting with dichloromethane:methanol (97:3) to afford the product; TLC: R$_f$=0.40, dichloromethane:methanol (95:5); MS: m/z=558(M+1). Analysis for C$_{28}$H$_{30}$F$_3$N$_5$O$_4$.0.35 H$_2$O: Calculated: C, 59.64; H, 5.49; N, 12.42; Found: C, 59.64; H, 5.45; N, 12.19.

The starting material was prepared as follows.

a. 2-[6-Oxo-2-(4-fluorophenyl)-5-(N-trifluoroacetyl-N-methylamino)-1,6-dihydropyrimidin-1-yl]-N-[3,3-difluoro-1-isopropyl-2-oxo-3-(N-phenethylcarbamoyl)propyl]acetamide. To a solution of the compound described at Example 35 (0.43 g) in N,N-dimethylformamide (3.5 mL) was added sodium carbonate (0.2 g) and iodomethane (0.310 mL). After overnight stirring, the reaction mixture was partitioned between dichloromethane and water. The aqueous phase was extracted with ethyl acetate, and the resulting emulsion was dispersed with salt. The organic phases were washed (brine), combined, dried and evaporated. Purification by chromatography, eluting with chloroform:methanol (40:1) afforded the product; TLC: R$_f$=0.16, chloroform:methanol (40:1); MS: m/z=654(M+1).

Example 48

R=benzyloxycarbonylamino; R$^4$=2-carboxyethyl; R$^6$=phenyl: The compound described at Example 28.b. was subjected to conditions similar to those described in Example 44, except after trituration the product was precipitated from hot ethyl acetate and ether with hexane to yield the title compound; TLC: R$_f$=0.32, dichloromethane:methanol:acetic acid (94:5:1); MS: m/z=628(M+1). Analysis for C$_{30}$H$_{31}$F$_2$N$_5$O$_8$.0.4 H$_2$O: Calculated: C, 56.76; H, 5.05; N, 11.03; Found: C, 56.72; H, 5.00; N, 10.89.

Example 49

R=isopropoxycarbonyl; R$^4$=methyl; R$^6$=phenyl: To a solution of the compound described at Example 18 (0.143 g) in tetrahydrofuran (2 mL) was added sodium carbonate (0.18 g) and isopropyl chloroformate (0.68 mL). After 18 hours, the mixture was diluted with ethyl acetate, washed (10% hydrochloric acid, saturated sodium bicarbonate, brine), dried, and evaporated. Chromatography, with chloroform:methanol (99:1) as the eluent, and trituration with ether and hexane yielded the title compound as a white solid (0.095 g); TLC: R$_f$=0.38, chloroform:methanol (96:4); MS: m/z=522 (m+1). Analysis for C$_{24}$H$_{29}$F$_2$N$_5$O$_6$: Calculated: C, 55.27; H, 5.60; N, 13.43; Found: C, 55.19; H, 5.64; N, 13.31.

Example 50

R=hydrogen; R$^4$=2-carboxyethyl; R$^6$=phenyl: The compound described at Example 48 was subjected to conditions similar to those described in Example 28. Chromatography, with chloroform:methanol:acetic acid (89.5:10:0.05) as the eluent, and concentration from chloroform:methanol:n-heptane gave the title compound; TLC: R$_f$=0.29, chloroform:methanol:acetic acid (94.5:5:0.5, developed twice); MS: m/z=494(M+1). Analysis for C$_{22}$H$_{25}$F$_2$N$_5$O$_6$.0.4 CHCl$_3$.0.1 H$_2$O: Calculated: C, 49.53; H, 5.08; N, 12.89; Found: C, 49.83; H, 4.85; N, 12.70.

Example 51

R=benzyloxycarbonylamino; R$^4$=2-(N,N-dimethylamino)ethyl; R$^6$=phenyl: To a solution of the compound described in part a. below (0.568 g) in dichloromethane (15 mL) was added trifluoroacetic acid (0.21 mL) and 1,1,1-triacetoxy-2,1-benzoxidol-3(3H)-one (1.15 g) for hour. The reaction was quenched with an aqueous solution of sodium bicarbonate and sodium thiosulfate, then diluted with ethyl acetate. After separation, the organic portion was washed (aqueous solution of sodium bicarbonate and sodium thiosulfate, saturated sodium bicarbonate, brine), dried, and evaporated. Chromatography, with dichloromethane:methanol (gradient, 97:3, 95:5, 92:8), yielded the title compound as a white solid (0.425 g); TLC: R$_f$=0.29, dichloromethane:methanol (95:5); MS: m/z=627(M+1). Analysis for C$_{31}$H$_{36}$F$_2$N$_6$O$_6$.0.7 H$_2$O: Calculated: C, 58.24; H, 5.90; N, 13.15; Found: C, 58.38; H. 5.71; N, 12.92.

The starting alcohol was prepared as follows.

a. 2-[5-Benzyloxycarbonylamino-6-oxo-2-phenyl-1,6-dihydropyrimidin-1-yl]-N-[3,3-difluoro-1-isopropyl-2-hydroxy-3-[N-[2-(N,N-dimethylamino)ethyl]carbamoyl]propyl]acetamide. The reaction was performed as described in Example 1.c. except that N,N-dimethylethylenediamine was used in place of propylamine and the reaction mixture was evaporated. The residue was dissolved in ethyl acetate, washed (saturated sodium bicarbonate, brine), dried, and evaporated. Chromatography, with dichloromethane:methanol (gradient, 97;3, 95:5, 93:7, 90:10) as eluent, yielded the alcohol; TLC: R$_f$=0.12, dichloromethane:methanol (95:5); MS: m/z=629(M+1).

Example 52

R=4-acetamidophenylsulfonyl; R$^4$=2-(4-pyridyl)ethyl; R$^6$=phenyl: To a solution of the compound described at Example 30 (0.226 g) in dichloromethane (4 mL) was added pyridine (0.17 mL) and 4-acetamidobenzenesulfonyl chloride (0.20 g). After 18 hours, the reaction mixture was diluted with ethyl acetate, washed (saturated sodium bicarbonate, brine), dried, and evaporated. Chromatography, with dichloromethane:methanol (gradient, 99:1, 97:3, 95:5, 93:7) as the eluent, and precipitation from hot ethyl acetate with petroleum ether gave the title compound as a white solid (0.176 g); TLC: R$_f$=0.17, chloroform:methanol (98:2); MS: m/z=724 (m+1). Analysis for C$_{34}$H$_{35}$F$_2$N$_7$O$_7$S.0.6 H$_2$O: Calculated: C, 55.59; H, 4.97; N, 13.35; Found: C, 55.52; H, 4.95; N, 13.18.

Example 53

R=4-acetamidophenylsulfonyl; R$^4$=2-morpholinoethyl; R$^6$=phenyl: The reaction was performed as described in Example 52, except starting with the compound described at Example 19. The product was purified by chromatography (first column) with chloroform:methanol:concentrated ammonium hydroxide (99.5:4:0.5) and chloroform:ethanol:methanol (88:8:4) as eluent, and (second column) with chloroform:methanol:concentrated ammonium hydroxide (89.5:10:0.5) and chloroform:ethanol:methanol (87:8:5). The recovered solids were triturated with ethyl acetate/petroleum ether to give the product as a white solid; TLC: $R_f=0.40$, chloroform:methanol:concentrated ammonium hydroxide (94.5:5:0.5, developed twice) and chloroform:ethanol:methanol (87:8:5); MS: m/z=732(M+1). Analysis for $C_{33}H_{39}F_2N_7O_8S$: Calculated: C, 54.16; H, 5.37; N, 13.40; Found: C, 53.77; H, 5.41; N, 13.25.

Example 54

R=benzyloxycarbonylamino; $R^A$=2-(N-phenylsulfonylcarbamoyl)ethyl; $R^6$=phenyl: To a solution of the compound described at Example 48 (0.35 g) in tetrahydrofuran (5 mL) was added triethylamine (0.48 mL), dimethylaminopyridine (0.21 g), 1-ethyl-3-(3-dimethylaminopropyl)carbodimide hydrochloride (0.103 g) and benzenesulfonamide (0.43 g). After 18 hours the reaction mixture was diluted with ethyl acetate, washed (10% hydrochloric acid, brine), dried, and evaporated. Chromatography, with chloroform:methanol (gradient, 97:3, 95:5, 92:8) as the eluent, and trituration with ethyl acetate:petroleum ether yielded the title compound as a white solid (0.081 g); TLC: $R_f=0.31$, chloroform:methanol (97:3) and chloroform:methanol:acetic acid (96:3:1); MS: m/z=767(M+1). Analysis for $C_{36}H_{36}F_2N_6O_9S \cdot 1.0\ H_2O$: Calculated: C, 55.10; H, 4.88; N, 10.71; Found: C, 54.02; H, 4.76; N, 10.54.

Example 55

R=2,2,2-trifluoroethoxycarbonyl; $R^A$=2-(4-pyridyl)ethyl; $R^6$=4-fluorophenyl: To a cooled solution of the compound described at Example 15 (0.21 g) in dichloromethane (4 mL) was added pyridine (0.125 mL). 2,2,2-Trifluoroethyl chloroformate (0.12 mL) was then added, and the reaction was allowed to stand for 15 minutes. Chromatography, with chloroform:methanol (gradient 40:1, 30:1) as the eluent, gave the title compound; TLC: $R_f=0.16$, chloroform:methanol (40:1); MS: m/z=671(M+1). Analysis for $C_{29}H_{28}F_6N_6O_6$: Calculated: C, 51.94; H, 4.21; N, 12.53; Found: C, 51.66{H, 4.65{N, 11.76.

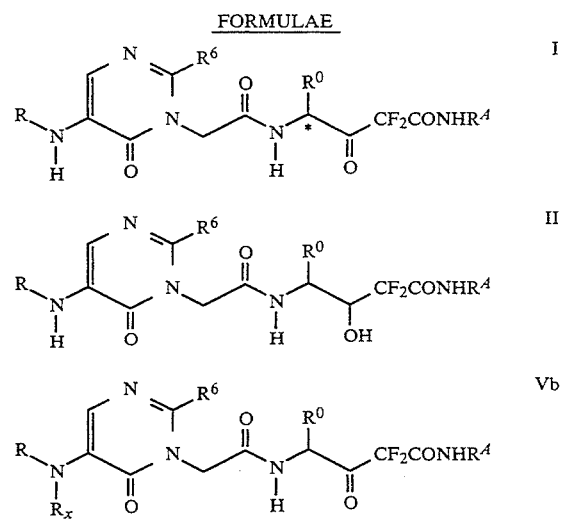

FORMULAE

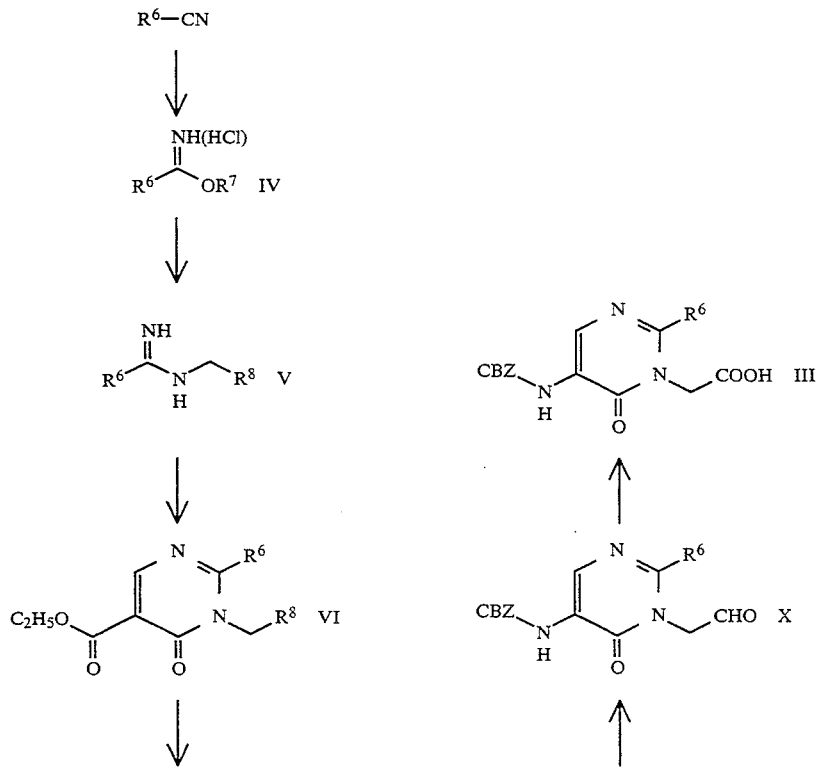

Scheme I

Scheme I
-continued
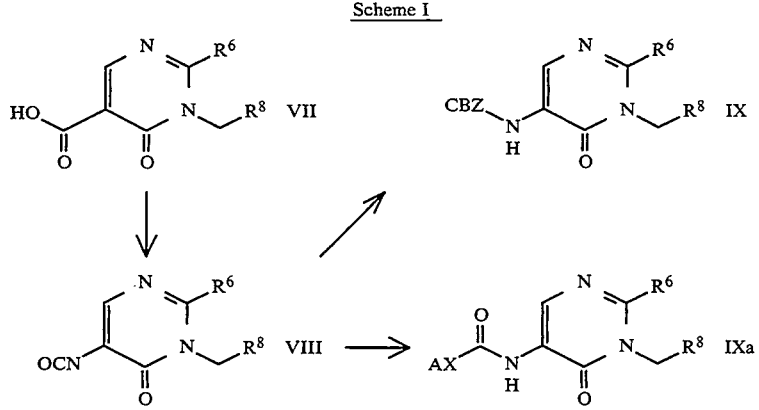
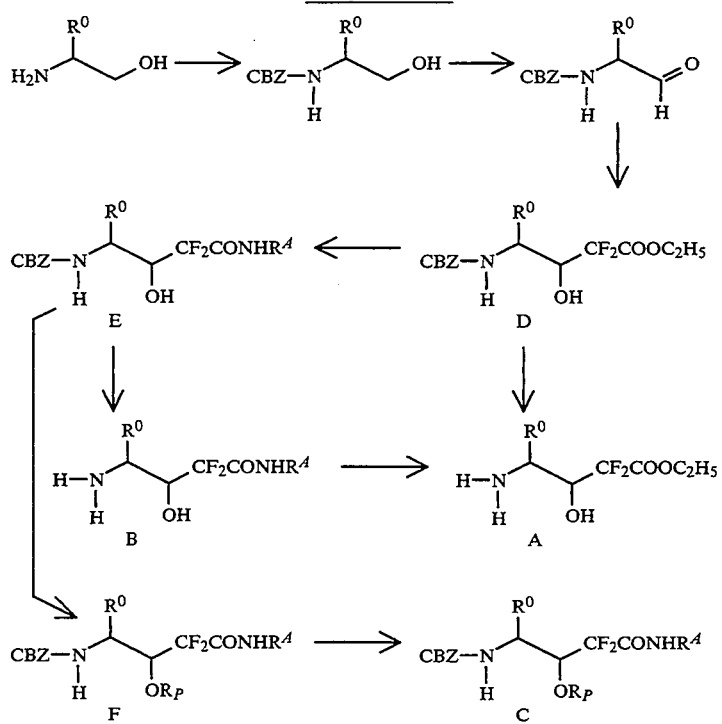
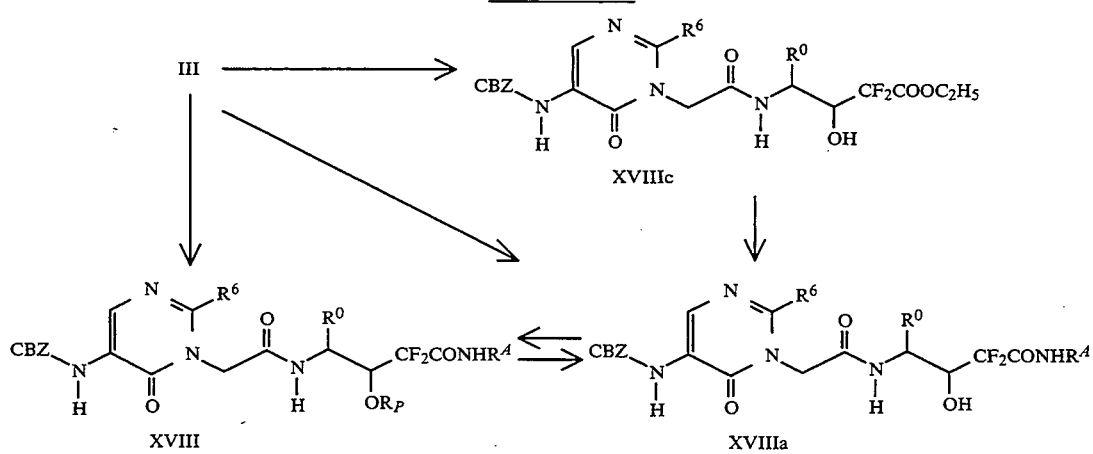

-continued
SCHEME II

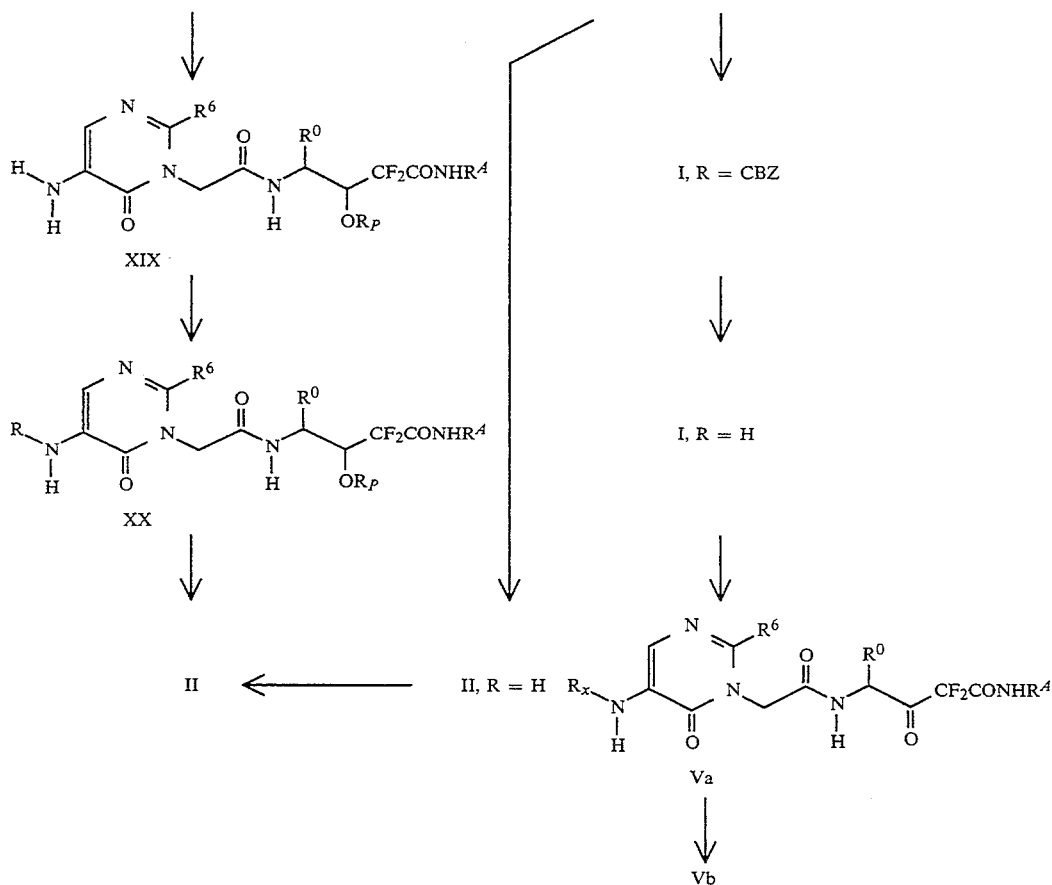

What is claimed is:

1. A compound of formula I (formula set out hereinbelow) wherein:

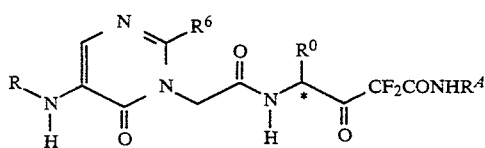

$R^0$ is (1–5C)alkyl;
R is hydrogen; or
R is an acyl group of formula A.X.CO- in which A.X-, taken together, is hydrogen, trifluoromethyl, 2,2,2-trifluoroethoxy, amino, methoxyamino, 2,2,2-trifluoroethylamino, RbRcN.O-, RaOCONH-, $R^1SO_2NH$-, RaOCO-, RbRcNCO- or RaCO-; or
R is an acyl group of formula A.X.CJ- in which
J is oxygen or sulfur;
X is a direct bond, imino, oxy or thio; and
A is as defined below or
A is tetrahydropyran-4-yl, 1-methylpiperid-4-yl, or 5-methyl-1,3-dioxacyclohex-5-ylmethyl; or
R is a sulfonyl group of formula D.W.$SO_2$- in which
D.W-, taken together, is hydroxy, amino, di(lower alkyl)amino, 2,2,2-trifluoroethylamino, 2,2,2-trifluoroethyl, 3,3,3-trifluoropropyl or trifluoromethyl; or
W is a direct bond, imino, carbonylimino, oxycarbonylimino or iminocarbonylimino; and D is as defined below; or
R is a group G as defined below;
The group A, D or G is (1–6C)alkyl, (3–6C)cycloalkyl, (3–6C)cycloalkyl-(1–3C)alkyl, aryl, aryl(1–3C)alkyl, heteroaryl or heteroaryl(1–3C)-alkyl wherein an aryl or heteroaryl moiety may bear one or more halogeno, nitro, methyl or trifluoromethyl groups and further wherein the group A, D or G may bear one or more substituents selected from a group consisting of hydroxy, lower alkoxy, lower acyloxy, COORa, $CH_2COORa$, CONRbRc, $CH_2CONRbRc$, $COO(CH_2)_2NReRf$, cyano, $SO_2R^1$, $CONRdSO_2R^1$, NReRf, NRgCHO, $NRgCOR^2$, $NRgCOOR^2$, NRhCQNRiRj, $NRkSO_2R^3$, $SO_2NRlRm$, $SO_2NRnCOR^4$ and $P(O)(ORa)_2$ in which
Q is oxygen or sulfur;
Ra–Rn are independently hydrogen, benzyl or lower alkyl; or, independently, a group NRbRc, NReRf, NRiRj or NRlRm is a cyclic radical selected from a group consisting of 1-pyrrolidinyl, piperidino, morpholino or 1-piperazinyl which may bear a lower alkyl substituent at the 4-position; or independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and
$R^1$–$R^4$ are independently trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl;

$R^6$ is (1–5C)alkyl which has no tertiary carbon, (3–7C)cycloalkyl, aryl or heteroaryl, which aryl or heteroaryl independently may bear one or more of the substituents defined for the group A or an aryl or heteroaryl moiety thereof;

$R^A$ is hydrogen, (1–6C)alkyl, (3–6C)cycloalkyl, (3–6C)cycloakyl(1–3C)alkyl, aryl(1–3C)alkyl, or heteroaryl(1–3C)alkyl, wherein an aryl or heteroaryl may bear one or more halogeno, methyl or trifluoromethyl group and further wherein the group $R^A$ may bear one or more substituents selected from a group consisting of hydroxy, lower alkoxy, COORs, CONRtRu, SO₂Rv, CONHSO₂Rv, NRtRu, NRsCHO, NRsCORv, NRsCOORv, NRsCONRtRu, NRsSO₂Rv, SO₂NRtRu, SO₂NRsCORv, and P(O)(ORv)₂ in which Rs-Ru are independently hydrogen, benzyl or lower alkyl, or, independently, a group NRtRu is a cyclic radical selected from a group consisting of 1-pyrrolidinyl, piperidino, morpholino or 1-piperazinyl which may bear a lower alkyl group at the 4-position; and Rv is trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl; and provided that no sp³ carbon is bonded to more than one nitrogen or oxygen, except as part of a cyclic ketal or where the nitrogen bears a carbonyl group; or, for a compound of formula I which is acidic or basic, a pharmaceutically acceptable salt thereof.

2. A compound as claimed in claim 1 wherein $R^0$ is methyl, ethyl, propyl, isopropyl or isobutyl; W is a direct bond or imino; G is (1–3C)alkyl, aryl(1–C)alkyl or heteroaryl(1–2C)alkyl which may bear one or more substituents as defined in claim 1 for G or a part thereof;

(1–6C)alkyl is methyl, ethyl, propyl, isopropyl, butyl, isobutyl, t-butyl, pentyl, 3-methylbutyl, 1-ethylpropyl, hexyl or 4-methylpentyl; (3–6C)cycloalkyl is cyclopropyl, cyclopentyl or cyclohexyl; the (1–3C)alkyl portion of (3–6C)cycloalkyl(1–3C)alkyl, aryl(1–3C)alkyl or heteroaryl(1–3C)alkyl is methylene, ethylene or trimethylene; aryl is phenyl, indenyl or naphthyl; heteroaryl is furyl, imidazolyl, tetrazolyl, pyridyl (or its N-oxide), thienyl, pyrimidinyl (or its N-oxide), indolyl or quinolinyl (or its N-oxide); lower alkyl is methyl, ethyl, propyl, isopropyl, butyl, isobutyl or t-butyl; lower acyloxy is acetoxy; lower alkoxy is methoxy, ethoxy, propoxy, isoproxy or t-butoxy; halogeno is bromo, chloro or fluoro;

COORa is carboxy or methoxycarbonyl; CONRbRc is carbamoyl or N,N-dimethylcarbamoyl; NRgCOR² is trifluoroacetylamino; CONRdSO₂R¹ is N-phenylsulfonylcarbamoyl or N-(4-chlorophenylsulfonyl)carbamoyl; A.X-, taken together, is tris(hydroxymethyl)methylamino, tris(acetoxymethyl)methylamino or 2,2-bis(hydroxymethyl)propoxy;

$R^6$ is, isopropyl, cyclopentyl, cyclohexyl, phenyl, furyl, thienyl or pyridyl in which a phenyl or heteroaryl may bear one or two substitutes as defined in claim 1 for $R^6$; and $R^A$ is hydrogen, methyl, ethyl, propyl, 2-(3–6C)cycloalkyl)ethyl, phenethyl, 2-(pyridyl)ethyl, (wherein the phenyl or pyridyl group may bear one or two halogeno or methyl groups and further wherein the group $R^A$ may bear a substituent selected from hydroxy, methoxy, carboxy, methoxycarbonyl, ethoxycarbonyl, carbamoyl, methylsulfonyl, N-methsulfonylcarbamoyl, N-phenylsulfonylcarbamoyl, amino, and dimethylamino) or 2-(dimethylamino)ethyl, 2-morpholinoethyl, 2-piperidinoethyl or 2-(4-methylpiperazin-1-yl)ethyl.

3. A compound as claimed in claim 2 wherein $R^0$ is isopropyl; J is oxygen; X is a direct bond, imino or oxy; A is methyl, ethyl, phenyl, benzyl, phenethyl, pyridyl, thienyl, 5-tetrazolyl, thiazolyl, pyridylmethyl, thenyl, 5-tetrazolylmethyl, 2-(pyridyl) ethyl, 2-(thienyl)ethyl or 2-(thiazolyl)ethyl wherein the phenyl or heteroaryl group may bear one or two halogeno or methyl groups and further wherein the group A may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, amino, dimethylamino, oxazolidin-2-on-3-yl, acetylamino, trifluoroacetylamino, ureido, methylsulfonyl, sulfamoyl, dimethylphosphoryl or diethylphosphoryl; D is methyl, ethyl, isopropyl, tert-butyl, cyclohexyl, phenyl, benzyl, phenethyl, pyridyl, thienyl, 5-tetrazolyl, thiazolyl, quinolinyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group D may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, N-(4-chlorophenylsulfonyl)carbamoyl, methylsulfonylamino, amino, dimethylamino, oxazolidin-2-on-3-yl, acetylamino, trifluoroacetylamino, ureido, methylsulfonyl, sulfamoyl, dimethylphosphoryl or diethylphosphoryl; and G is methyl, ethyl, benzyl, phenethyl, pyridyl, pyridylmethyl, thenyl, 5-tetrazolylmethyl, or 2-(pyridyl)ethyl, wherein the phenyl or heteroaryl group may bear one or two halogeno or methyl groups and further wherein the group G may bear a substituent selected from hydroxy, methoxy, acetoxy, carboxy, methoxycarbonyl, ethoxycarbonyl, carbamoyl, dimethylcarbamoyl, phenylcarbamoyl, pyridylcarbamoyl, methylsulfonylamino, amino, dimethylamino, acetylamino, nicotinoylamino, or trifluoroacetylamino.

4. A compound as claimed in claim 1, 2 or 3 wherein R is hydrogen, trifluoroacetyl, hydroxyoxalyl, methoxycarbonyl, ethoxycarbonyl, isopropoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl, 2-dimethylaminoethoxycarbonyl, acetyl, carbamoylmethylaminocarbonyl, 4-(N-phenylsulfonylcarbamoyl)phenylacetyl, sulfo, aminosulfonyl, dimethylaminosulfonyl, trifluoromethylsulfonyl, methylsulfonyl (which may bear a methoxycarbonyl, carboxy or ethylsulfonyl substituent), methylaminosulfonyl, isopropylaminosulfonyl, butylsulfonyl, butylaminosulfonyl, tert-butylaminosulfonyl, cyclohexylaminosulfonyl, phenylsulfonyl (in which the phenyl may bear a chloro, nitro, amino, acetylamino, trifluoroacetylamino, methoxy, carboxy, N-(4-chlorophenylsulfonyl)carbamoyl, or methylsulfonylamino substituent at the 3- or 4-position), anilino, pyridylsulfonyl, quinolinylsulfonyl, benzylsulfonyl (in which the phenyl ring may bear a nitro or amino substituent at the 3- or 4-position), pyridylmethylsulfonyl, 2-(pyridyl)ethylsulfonyl, benzylaminosulfonyl, methyl, ethyl, benzyl, phenethyl or pyridylmethyl.

5. A compound as claimed in any one of claims 1-3 in which $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents.

6. A compound as claimed in claim 5 wherein $R^6$ is phenyl, 4-fluorophenyl or 2-thienyl.

7. A compound as claimed in claim 1 selected from 2-(5-benzyloxycarbonylamino-6-oxo-2-phenyl-1,6-dihydropyrimidin-1-yl)-N-[3,3-difluoro-1-isopropyl-2-oxo-3-(N-phenethylcarbamoyl)propyl]acetamide, 2-(5-amino-6-oxo-2-phenyl-1,6-dihydropyrimidin-1-yl)-N-[3,3-difluoro-1-isopropyl-2-oxo-3-(N-propylcarbamoyl)propyl]acetamide, 2-(5-amino-6-oxo-2-phenyl-1,6-dihydropyrimidin-1-yl)-N-[3,3-difluoro-1-isopropyl-2-oxo-3-(N-phenethylcarbamoyl)propyl]acetamide and 2-[6-oxo-2-phenyl-5-(4-pyridylmethoxycarbonylamino)-1,6-dihydropyrimidin-1-yl]-N-[3,3-difluoro-1-isopropyl-2-oxo-3-(N-phenethylcarbamoyl)propyl]acetamide.

8. A salt as claimed in claim 1 selected from
(a) for an acidic compound of formula I, an alkalai metal salt, an alkaline earth metal salt, an aluminum salt, an ammonium salt, or a salt made from an organic base which affords a pharmaceutically acceptable cation; and
(b) for a basic compound of formula I, an acid-addition salt made with an acid which provides a pharmaceutically acceptable anion.

9. A compound of formula Vb, set out hereinbelow, or a salt thereof

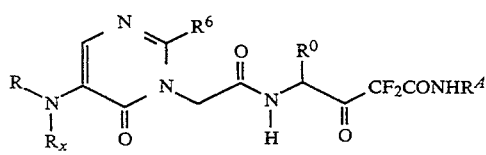

Vb wherein:
R is (1–6C) alkyl, (3–6C)cycloalkyl, (3–6C)cycloalkyl-(1–3C)alkyl, aryl, aryl(1–3C)alkyl, heteroaryl or heteroaryl(1–3C)-alkyl wherein an aryl or heteroaryl moiety may bear one or more halogeno, nitro, methyl or trifluoromethyl groups and further wherein the group A, D or G may bear one or more substituents selected from a group consisting of hydroxy, lower alkoxy, lower acyloxy, COORa, CH2COORa, CONRbRc, CH2CONRbRc, COO(CH2)2NReRf, cyano, SO2R1, CONRdSO2R1, NReRf, NRgCHO, NRgCOR2, NRgCOOR2, NRhCQNRiRj, NRkSO2R3, SO2NRlRm, SO2NRnCOR4 and P(O)(ORa)2 in which Q is oxygen or sulfur;

Ra-Rn are independently hydrogen, benzyl or lower alkyl; or, independently, a group NRbRc, NReRf, NRiRj or NRlRm is a cyclic radical selected from a group consisting of 1-pyrrolidinyl, piperidino, morpholino or 1-piperazinyl which may bear a lower alkyl substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^4$-$R^4$ are independently trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl;

$R^A$ is hydrogen, (1–6C)alkyl, (3–6C)cycloalkyl, (3–6C)cycloalkyl(1–3C)alkyl, aryl(1–3C)alkyl, or heteroaryl(1–3C)alkyl, wherein an aryl or heteroaryl may bear one or more halogeno, methyl or trifluoromethyl group and further wherein the group $R^A$ may bear one or more substituents selected from a group consisting of hydroxy, lower alkoxy, COORs, CONRtRu, SO2Rv, CONHSO2Rv, NRtRu, NRsCHO, NRsCORv, NRsCOORv, NRsCONRtRu, NRsSO2Rv, SO2NRtRu, SO2NRsCORv, and P(O)(ORv)2 in which Rs-Ru are independently hydrogen, benzyl or lower alkyl, or, independently, a group NRtRu is a cyclic radical selected from a group consisting of 1-pyrrolidinyl, piperidino, morpholino or 1-piperazinyl which may bear a lower alkyl group at the 4-position; and Rv is trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl; and $R^0$ is (1–5C)alkyl;

$R^6$ is (1–5C)alkyl which has no tertiary carbon, (3–7C)cycloalkyl, aryl or heteroaryl, which aryl or heteroaryl independently may bear one or more of the substituents defined for the group A or an aryl or heteroaryl moiety thereof;

and Rx is a group which protects and activates a primary amino group for substitution.

10. A pharmaceutical composition comprising a compound as defined in claim 1, or a pharmaceutically acceptable salt thereof, and a pharmaceutically acceptable diluent or carrier.

11. A method of administering a compound of claim 1, or a pharmaceutically acceptable salt thereof, to a human is need thereof for treatment of a disease or condition in which human leukocyte elastase is implicated.

* * * * *